United States Patent [19]

Shoshi et al.

[11] Patent Number: 5,072,043

[45] Date of Patent: Dec. 10, 1991

[54] STYRENE DERIVATIVES AND ELECTROPHOTOGRAPHIC PHOTOCONDUCTOR COMPRISING ONE OF THE STYRENE DERIVATIVES

[75] Inventors: Masayuki Shoshi, Numazu; Masaomi Sasaki, Susono, both of Japan

[73] Assignee: Ricoh Company, Ltd., Tokyo, Japan

[21] Appl. No.: 545,124

[22] Filed: Jun. 27, 1990

Related U.S. Application Data

[60] Continuation of Ser. No. 403,055, Sep. 5, 1989, abandoned, which is a continuation of Ser. No. 839,965, Mar. 17, 1986, abandoned, which is a division of Ser. No. 646,064, Aug. 31, 1984, Pat. No. 4,603,097.

[30] Foreign Application Priority Data

| Oct. 28, 1983 | [JP] | Japan | 58-201021 |
| Oct. 28, 1983 | [JP] | Japan | 58-201022 |
| Oct. 28, 1983 | [JP] | Japan | 58-201023 |
| Oct. 28, 1983 | [JP] | Japan | 58-201024 |
| Oct. 28, 1983 | [JP] | Japan | 58-201025 |
| Oct. 28, 1983 | [JP] | Japan | 58-201026 |

[51] Int. Cl.⁵ .............. C07C 211/00; C07C 321/00; C07C 255/00; C07C 229/00
[52] U.S. Cl. .................... 564/305; 564/440; 564/441; 564/442; 564/443; 558/418; 562/457; 560/19
[58] Field of Search ........... 564/315, 305, 440, 441, 564/442, 443; 549/68; 558/418; 562/457; 560/19

[56] References Cited

U.S. PATENT DOCUMENTS

| 3,158,475 | 11/1964 | Cassiers et al. | 430/97 |
| 3,246,983 | 4/1966 | Sus et al. | 430/97 |
| 3,677,752 | 7/1972 | Looker et al. | 564/315 |
| 3,852,065 | 12/1974 | Hectors | 430/74 |
| 4,515,883 | 5/1985 | Sasaki | |
| 4,572,884 | 2/1986 | Sasaki | |
| 4,603,097 | 7/1986 | Shoshi et al. | 430/73 |

Primary Examiner—Alan Siegel
Attorney, Agent, or Firm—Oblon, Spivak, McClelland, Maier & Neustadt

[57] ABSTRACT

Styrene derivatives of the formula

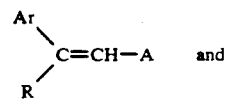

an electrophotographic photoconductor comprising an electroconductive support material and a photosensitive layer comprising at least one styrene derivatives of the same formula are disclosed, in which Ar represents an unsubstituted of substituted phenyl group or an unsubstituted or substituted styryl group, R represents hydrogen, a lower alkyl group or an unsubstituted or substituted phenyl group, and A is selected from the group consisting of

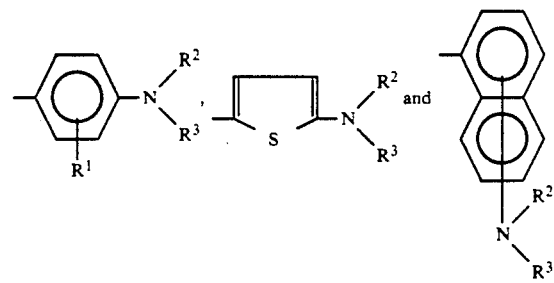

wherein $R^1$ represents a lower alkyl group or a lower alkoxy group, $R^2$ and $R^3$ each represents a lower alkyl group, an aralkyl group, or an unsubstituted or substituted phenyl group.

2 Claims, 4 Drawing Sheets

STYRENE DERIVATIVES AND ELECTROPHOTOGRAPHIC PHOTOCONDUCTOR COMPRISING ONE OF THE STYRENE DERIVATIVES

This application is a Continuation of application Ser. No. 07/403,555, filed on Sept. 5, 1989, now abandoned, which is a continuation of application Ser. No. 06/839,965, filed Mar. 17, 1986, now abandoned, which is a divisional of application Ser. No. 06/646,064, filed Aug. 31, 1984, now U.S. Pat. No. 4,603,097.

BACKGROUND OF THE INVENTION

The present invention relates to styrene derivatives and an electrophotographic photoconductor comprising a photosensitive layer containing at least one of the styrene derivatives overlayed on an electroconductive support material.

Conventionally, a variety of inorganic and organic electrophotographic photoconductors are known. As inorganic photoconductors for use in electrophotography, there are known types, in which the photoconductive material is, for instance, selenium, cadmium sulfide and zinc oxide. In an electrophotographic process, a photoconductor is first exposed to corona charges in the dark, so that the surface of the photoconductor is electrically charged uniformly. The thus uniformly charged photoconductor is then exposed to original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made, for instance, of a polymeric material; thus, visible developed images can be obtained on the photoconductor. It is necessary that photoconductors for use in electrophotography have at least the following fundamental properties: (1) chargeability to a predetermined potential in the dark; (2) minimum electric charge dissipation in the dark; and (3) quick dissipation of electric charges upon exposure to light.

While the above-mentioned inorganic electrophotographic photoconductors have many advantages over other conventional electrophotographic photoconductors, at the same time they have several shortcomings from the viewpoint of practical use.

For instance, a selenium photoconductor, which is widely used at present, has the shortcoming that its production is difficult and, accordingly, its production cost is high. Further, it is difficult to work it into the form of a belt due to its poor flexibility, and it is so vulnerable to heat and mechanical shocks that it must be handled with the utmost care.

Cadmium sulfide photoconductors and zinc oxide photo-conductors are prepared by dispersing cadmium sulfide or zinc oxide in a binder resin. They can be produced inexpensively compared with selenium photoconductors and are also used commonly in practice. However, the cadmium sulfide and zinc oxide photoconductors are poor in surface smoothness, hardness, tensile strength and wear resistance. Therefore, they are not suitable as photoconductors for use in plain paper copiers in which the photoconductors are used in quick repetition.

Recently, organic electrophotographic photoconductors, which are said not to have such shortcomings of the inorganic electrophotographic photoconductors, have been proposed, and some of them are in fact employed for practical use. Representative examples of such organic electrophotographic photoconductors are an electrophotographic photoconductor comprising poly-N-vinylcarbazole and 2,4,7-trinitro-fluorene-9-one (U.S. Pat. No. 3,484,237); a photoconductor in which poly N-vinylcarbazole is sensitized by a pyrylium salt type dyestuff (Japanese Patent Publication No. 48-25658); a photoconductor containing as the main component an organic pigment (Japanese Laid-Open Patent Application No. 47-37543); and a photoconductor containing as the main component an eutectic crystaline complex (Japanese Laid-Open Patent Application No. 47-10735).

Although the above-mentioned organic electrophotographic photoconductors have many advantages over other conventional electrophotographic photoconductors, they still have several shortcomings from the viewpoint of practical use, in particular, in terms of cost, production, durability and electrophotographic sensitivity.

SUMMARY OF THE INVENTION

It is therefore an object of the present invention to provide styrene derivatives, and an electrophotographic photoconductor or element comprising a photosensitive layer containing at least one of the styrene derivatives overlayed on an electroconductive support material, having high photosensitivity, which does not give rise to difficulties in producing the electrophotographic photoconductor, and which is comparatively inexpensive and excellent in durability.

The styrene derivatives employed in the present invention are represented by the following general formula (I):

wherein Ar represents an unsubstituted or substituted phenyl group, or an unsubstituted or substituted styryl group, R represents hydrogen, a lower alkyl group or an unsubstituted or substituted phenyl group, and A represents

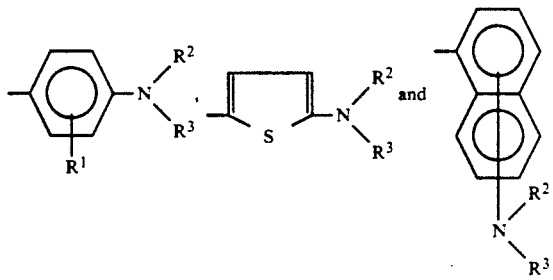

wherein $R^1$ represents a lower alkyl group or a lower alkoxy group, $R^2$ and $R^3$ each represent a lower alkyl group, an aralkyl group, or an unsubstituted or substituted phenyl group.

DETAILED DESCRIPTION OF THE PREFERRED EMBODIMENTS

Figure 1:
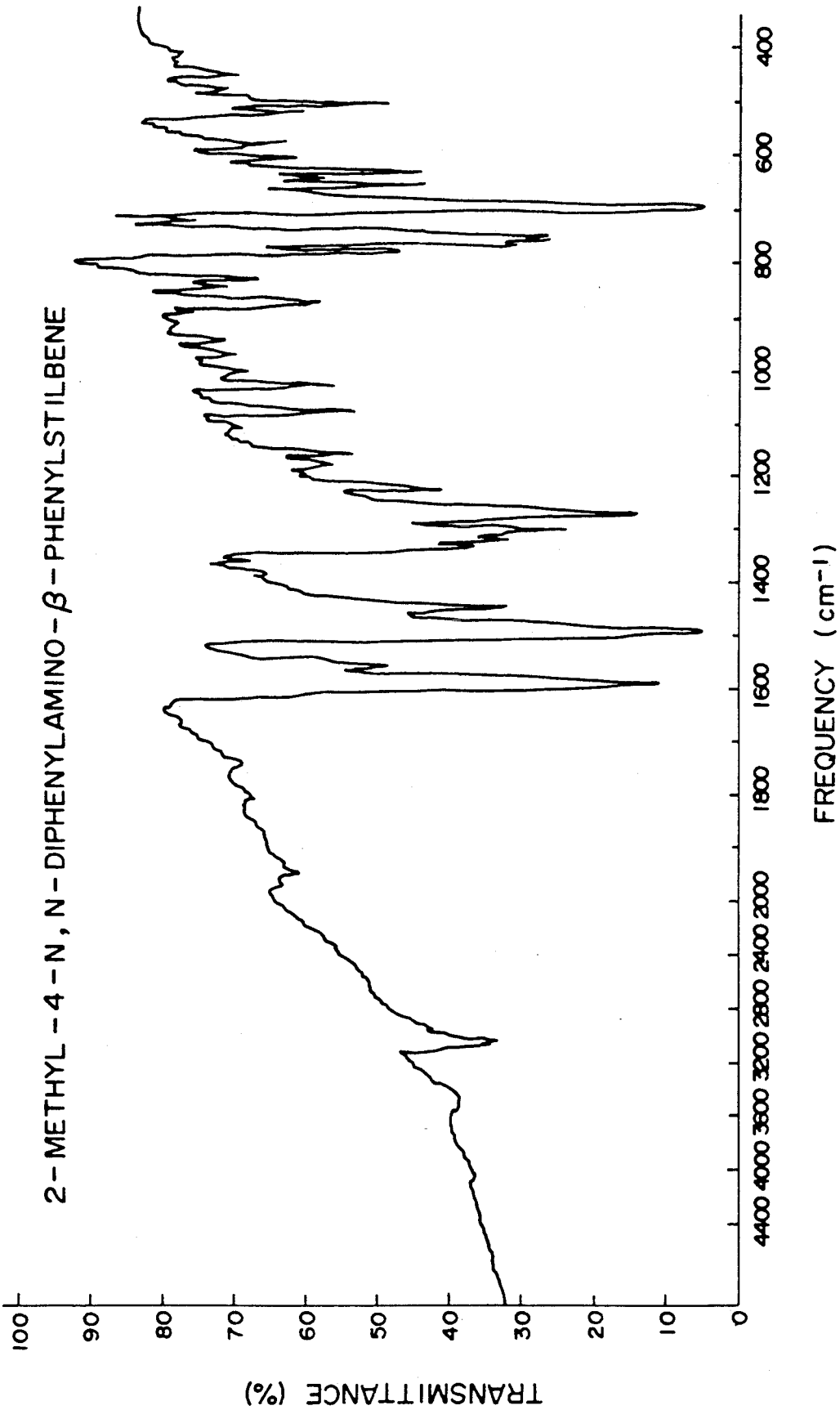
FIG. 1 is an infrared spectrum of 2-methyl-4-N, N-diphenylamino-β-phenylstilbene.

The electrophotographic photoconductor according to the present invention comprises a photosensitive layer which contains at least one of the styrene derivatives of the above mentioned formula (I), overlayed on an electroconductive support material.

Of the styrene derivatives of the previously described formula (I), stilbene-type derivatives of the following formula (Ia), in which A is

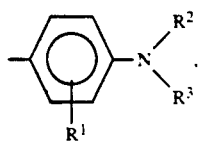

can be synthesized by reacting a phenyl derivative of formula (IIa) with an aldehyde compound of formula (IIIa):

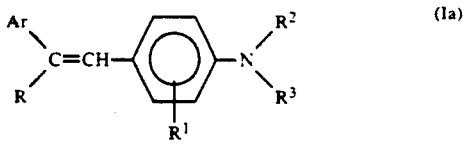

wherein Ar represents an unsubstituted or substituted phenyl group or an unsubstituted or substituted styryl group, R represents hydrogen, a lower alkyl group or an unsubstituted or substituted phenyl group, $R^1$ represents a lower alkyl group or a lower alkoxy group, $R^2$ and $R^3$ each represent a lower alkyl group, a lower aralkyl group, or an unsubstituted or substituted phenyl group,

wherein Ar and R are respectively the same as those defined in the formula (Ia). Y represents a triphenylphosphonium group of the formula

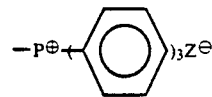

in which $Z^\ominus$ represents a halogen; or a dialkoxyphosphorous group of the formula $-P(OR^4)_2$ in which $R^4$ represents a lower alkyl group,

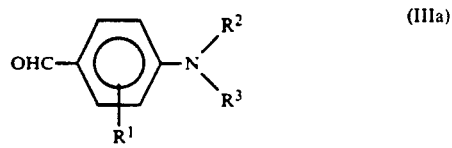

wherein $R^1$, $R^2$ and $R^3$ are respectively the same as those defined in the formula (Ia).

Preparation of the stilbene-type derivative of the previously described formula (Ia) will now be explained.

In the preparation, the phenyl derivative of the formula (IIa) can be prepared without difficulty by heating a corresponding halomethyl compound and a trialkylphosphite or triphenylphosphite without using any solvent or using a solvent, such as toluene, tetrahydrofuran or N,N-dimethylformamide. As the trialkylphosphite, those having alkyl groups with 1 to 4 carbon atoms, in particular, those having methyl groups or ethyl groups are preferable.

The thus prepared phenyl derivative of the formula (IIa) is allowed to react with the aldehyde compound of the formula (IIIa) in the presence of a basic catalyst at temperatures ranging from room temperature to about 100° C.

As the basic catalyst for the above reaction, sodium hydroxide, potassium hydroxide, sodium amide, sodium hydride, and alcoholates such as sodium methylate and potassium-tert-butoxide, can be employed.

As the reaction solvent, the following can be employed: methanol, ethanol, isopropanol. butanol, 2-methoxyethanol, 1,2-dimethoxyethane, bis(2-methoxyethyl) ether, dioxane, tetrahydrofuran, toluene, xylene, dimethyl sulfoxide, N,N-dimethylformamide, N-methylpyrrolidone and 1,3-dimethyl-2-imidazolidinone.

Of the above solvents, polar solvents, for example, N,N-dimethylformamide and dimethyl sulfoxide are particularly suitable for this reaction.

The reaction temperature for the above reaction can be set in a relatively wide range, depending upon (i) the stability of the solvent employed in the presence of the basic catalyst, (ii) the reactivities of the condensation components, that is, the phenyl derivative of the formula (IIa) and the aldehyde compound of the formula (IIIa), and (iii) the reactivity of the basic catalyst which works as a condensation agent in this reaction. For example, when a polar solvent is employed as the reaction solvent, the reaction temperature is preferably set in the range of from room temperature to about 100° C., more preferably in the range of from room temperature to about 80° C. However, if it is desired to shorten the reaction time or when a less amount of the reactive condensation agent is employed, the reaction temperature can be elevated beyond the aforementioned range.

In the thus prepared styrene derivative of the formula (Ia),

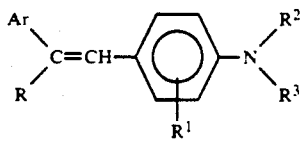

the preferable substituents of the phenyl group in Ar and R are, for example, an alkyl group such as methyl, ethyl, propyl and butyl; an alkoxy group such as methoxy, ethoxy, propoxy and butoxy; a phenoxy group, a benzyloxy group; halogen such as chlorine and bromine; and the preferable substituents of the phenyl group in $R^2$ and $R^3$ are, for example, an alkyl group such as methyl, ethyl, propyl, and butyl; an alkoxy group such as methoxy, ethoxy, propoxy and butoxy; a thioalkoxy group such as thiomethoxy and thioethoxy; a thiophenyl group; halogen such as chlorine and bromine; a dialkylamino group such as dimethylamino, diethylamino, dipropylamino and N-methyl-N-ethylamino; hydroxy group, a carboxy group and ester groups thereof, an acyl group; an aryloxy group such as phenoxy; an aralkyloxy group such as benzyloxy; a trifluoromethyl group; a nitro group; and a cyano group.

Preparation of the stilbene-type derivatives of the formula (Ia) will now be explained in detail by referring to the following examples:

SYNTHESIS EXAMPLE 1

30.40 g (0.1 mol) of diethyl 1,1-diphenylmethylphosphonate and 28.7 g of (0.1 mol) of 2-methyl-4-diphenylaminobenzaldehyde were dissolved in 500 ml of N,N-dimethylformamide. To this mixture, 16.8 g (0.15 mol) of potassium-tert-butoxide was added with the temperature of the reaction mixture maintained in the range of from 25° C. to 35° C. After the addition of the potassium-tert-butoxide, the mixture was stirred at room temperature for 6 hours and was then diluted with 1 l of water. Powder separated from the reaction mixture was filtered, washed with water and dried, whereby light yellow powder was obtained. The yield was 37.1 g (85%). The thus obtained light yellow powder was recrystallized from a mixed solvent of methyl acetate and ethanol, whereby pure 2-methyl-4-N,N-diphenylamino-phenylstilbene was obtained. The melting point was 119.5 121.0° C.

An infrared spectrum of the 2-methyl-4-N,N-diphenylamino-β-phenylstilbene, taken by use of a KBr pellet, is shown in FIG. 1.

The results of the elemental analysis of the thus obtained 2-methyl-4-N,N-diphenylamino-8 -phenylstilbene were as follows:

|  | % C | % H | % N |
| --- | --- | --- | --- |
| Found | 90.62 | 6.21 | 3.23 |
| Calculated | 90.57 | 6.23 | 3.20 |

The above calculation was based on the formula for 2-methyl-4-N,N-diphenylamino-β-phenylstilbene of $C_{33}H_{27}N$.

SYNTHESIS EXAMPLES 2 THROUGH 6

Stilbene-type derivatives listed in Table 1 were prepared by the same method as in Synthesis Example 1.

TABLE 1

| Example No. | Stilbene Type Derivatives | Melting Point (°C.) | Elemental Analysis Found/Calculated | | |
| --- | --- | --- | --- | --- | --- |
| | | | % C | % H | % N |
| 2 | [structure] | 150.0–151.0 | 89.71/ 89.70 | 6.39/ 6.43 | 3.85/ 3.88 |
| 3 | [structure] | Oily Material | 89.61/ 89.55 | 6.69/ 6.72 | 3.69/ 3.73 |
| 4 | [structure] | 111.0–112.0 | 85.79/ 85.89 | 6.39/ 6.45 | 3.51/ 3.58 |
| 5 | [structure] | Oily Material | 89.48/ 89.55 | 6.70/ 6.72 | 3.64/ 3.73 |

TABLE 1-continued

| Example No. | Stilbene Type Derivatives | Melting Point (°C.) | Elemental Analysis Found/Calculated | | |
|---|---|---|---|---|---|
| | | | % C | % H | % N |
| 6 | 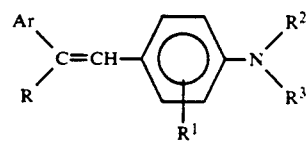 | 156.5–158.5 | 89.81/ 89.87 | 6.49/ 6.52 | 3.52/ 3.62 |

SYNTHESIS EXAMPLE 7

42.3 g (0.1 mol) of 4-chlorobenzyltriphenylphosphonium chloride and 28.7 g (0.1 mol) of 2-methyl-4-N,N-diphenyl-aminobenzaldehyde were dissolved in 500 ml of N,N-dimethylformamide. To this mixture, 16.8 g (0.15 mol) of potassium-tert-butoxide was added with the temperature of the reaction mixture maintained in the range of from 25° C. to 35° C. After the addition of the potassium-tert-butoxide, the reaction mixture was stirred at room temperature for 5 hours and was then diluted with 1 l of water. Powder separated from the reaction mixture was filtered, washed with water and dried, whereby light yellow powder was obtained. The yield was 38.8 g (98.0%) and the melting point of the product was 127.5~129.5° C.

Upon recrystallization of the powder from a mixed solvent of toluene and n-hexane in the presence of a small amount of iodine, 2-methyl-4-N,N-diphenylamino-4'-chlorostilbene precipitated as light yellow needle-like crystal. The yield was 30.6 g (77.4%). The melting point of the product was 129.3~130.5° C.

The results of the elemental analysis of the thus obtained 2-methyl-4-N,N-diphenylamino-4'-chlorostilbene were as follows:

| | % C | % H | % N | Cl % |
|---|---|---|---|---|
| Found | 81.72 | 5.57 | 3.54 | 9.00 |
| Calculated | 81.91 | 5.60 | 3.54 | 8.95 |

The above calculation was based on the formula for 2-methyl-4-N,N-diphenylamino-4'-chlorostilbene of $C_{27}H_{22}NCl$.

In addition to the stilbene-type derivatives described in Synthesis Exmaples 1 through 7, other stilbene-type derivatives of the formula (Ia), that is, $$\begin{matrix} Ar \\ \phantom{x} \\ R \end{matrix} C=CH-\underset{R^1}{\underset{|}{\bigcirc}}-N\begin{matrix} R^2 \\ \phantom{x} \\ R^3 \end{matrix}$$

which are also useful in the present invention, are listed in the following Table 2.

TABLE 2

$$\begin{matrix} Ar \\ \phantom{x} \\ R \end{matrix} C=CH-\underset{R^1}{\underset{|}{\bigcirc}}-N\begin{matrix} R^2 \\ \phantom{x} \\ R^3 \end{matrix}$$

Substituted Position: 2,3 on ring bearing $R^1$

| Compound No. | Ar | R | $R^1$ | $R^2$ | $R^3$ |
|---|---|---|---|---|---|
| 1 | phenyl | H | 2-CH₃ | phenyl | —C₂H₅ |
| 2 | phenyl | H | 2-CH₃ | phenyl | phenyl |
| 3 | phenyl | H | 2-CH₃ | 4-CH₃-phenyl | 4-CH₃-phenyl |

TABLE 2-continued
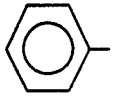
Substituted Position
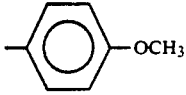
| Compound No. | Ar | R | R¹ | R² | R³ |
|---|---|---|---|---|---|
| 4 |  | H | 2-CH$_3$ | 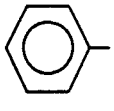 | 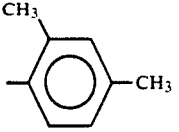 |
| 5 | 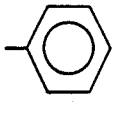 | H | 2-CH$_3$ | 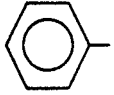 | 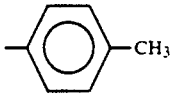 |
| 6 |  | H | 2-CH$_3$ |  | 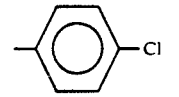 |
| 7 |  | H | 2-CH$_3$ | 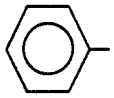 |  |
| 8 | 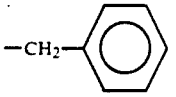 | H | 2-CH$_3$ | 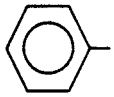 | —CH$_2$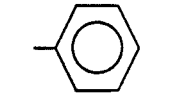 |
| 9 |  | H | 2-OCH$_3$ | 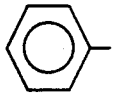 | 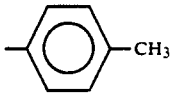 |
| 10 | 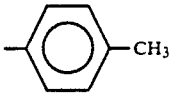 | H | 2-OCH$_3$ | 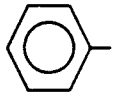 | 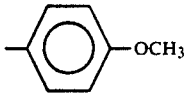 |
| 11 |  | H | 2-OCH$_3$ | 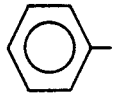 | 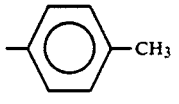 |
| 12 |  | H | 2-OCH$_3$ | 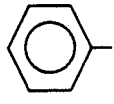 |  |
| 13 |  | H | 3-CH$_3$ | | |

TABLE 2-continued $$\text{Ar-C(R)=CH-C}_6\text{H}_3(\text{R}^1)\text{-N(R}^2)(\text{R}^3)$$

Substituted Position: 2, 3 on R¹ ring

| Compound No. | Ar | R | R¹ | R² | R³ |
|---|---|---|---|---|---|
| 14 | phenyl | H | 3-CH₃ | 4-CH₃-phenyl | 4-CH₃-phenyl |
| 15 | phenyl | H | 3-CH₃ | 4-OCH₃-phenyl | phenyl |
| 16 | phenyl | H | 3-OCH₃ | phenyl | phenyl |
| 17 | phenyl | H | 3-OCH₃ | 4-CH₃-phenyl | 4-CH₃-phenyl |
| 18 | 4-CH₃-phenyl | H | 2-CH₃ | phenyl | —C₂H₅ |
| 19 | 2-CH₃-phenyl | H | 2-CH₃ | phenyl | phenyl |
| 20 | 4-CH₃-phenyl | H | 2-CH₃ | 4-CH₃-phenyl | 4-CH₃-phenyl |
| 21 | 4-CH₃-phenyl | H | 2-CH₃ | 4-OCH₃-phenyl | 4-OCH₃-phenyl |
| 22 | 4-CH₃-phenyl | H | 2-CH₃ | 4-CH₃-phenyl | phenyl |
| 23 | 4-CH₃-phenyl | H | 2-CH₃ | 4-CN-phenyl | phenyl |

TABLE 2-continued $$\underset{R}{\overset{Ar}{>}}C=CH-\underset{R^1}{\overset{}{\bigcirc}}-N\underset{R^3}{\overset{R^2}{<}}$$

Substituted Position

| Compound No. | Ar | R | R¹ | R² | R³ |
|---|---|---|---|---|---|
| 24 | 2-methylphenyl | H | 2-OCH₃ | phenyl | –CH₂–phenyl |
| 25 | 2-methylphenyl | H | 2-CH₃ | phenyl | phenyl |
| 26 | 3-methylphenyl | H | 2-CH₃ | phenyl | phenyl |
| 27 | 4-methylphenyl | H | 2-CH₃ | phenyl | phenyl |
| 28 | 2-methylphenyl | H | 2-OCH₃ | phenyl | phenyl |
| 29 | 4-methylphenyl | H | 2-OCH₃ | 4-OCH₃-phenyl | 4-OCH₃-phenyl |
| 30 | 4-methylphenyl | H | 2-OCH₃ | 4-CH₃-phenyl | 4-CH₃-phenyl |
| 31 | 4-methylphenyl | H | 3-CH₃ | phenyl | phenyl |
| 32 | 4-methoxyphenyl | H | 2-CH₃ | phenyl | –C₂H₅ |
| 33 | 4-methoxyphenyl | H | 2-CH₃ | phenyl | phenyl |

TABLE 2-continued
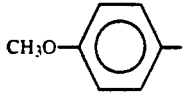
| Compound No. | Ar | R | Substituted Position R¹ | R² | R³ |
|---|---|---|---|---|---|
| 34 | 4-CH₃O-C₆H₄ | H | 2-CH₃ | 4-CH₃-C₆H₄ | 4-CH₃-C₆H₄ |
| 35 | 2-CH₃O-C₆H₄ | H | 2-CH₃ | 4-CH₃O-C₆H₄ | C₆H₅ |
| 36 | 4-CH₃O-C₆H₄ | H | 2-CH₃ | 2,4-(CH₃)₂-C₆H₃ | C₆H₅ |
| 37 | 4-CH₃O-C₆H₄ | H | 2-OCH₃ | C₆H₅ | C₆H₅ |
| 38 | 4-CH₃O-C₆H₄ | H | 2-OCH₃ | 4-CH₃-C₆H₄ | 4-CH₃-C₆H₄ |
| 39 | 4-CH₃O-C₆H₄ | H | 2-OCH₃ | 4-CH₃-C₆H₄ | C₆H₅ |
| 40 | 2-CH₃O-C₆H₄ | H | 3-CH₃ | C₆H₅ | C₆H₅ |
| 41 | 2-CH₃O-C₆H₄ | H | 2-CH₃ | C₆H₅ | C₆H₅ |
| 42 | 3-CH₃O-C₆H₄ | H | 2-CH₃ | C₆H₅ | C₆H₅ |

TABLE 2-continued

| Compound No. | Ar | R | Substituted Position R¹ | R² | R³ |
|---|---|---|---|---|---|
| 43 | 4-CH₃O-C₆H₄- | H | 2-CH₃ | C₆H₅- | C₆H₅- |
| 44 | 4-Cl-C₆H₄- | H | 2-CH₃ | C₆H₅- | —CH₃ |
| 45 | 4-Cl-C₆H₄- | H | 2-CH₃ | C₆H₅- | C₆H₅- |
| 46 | 2-Cl-C₆H₄- | H | 2-CH₃ | C₆H₅- | C₆H₅- |
| 47 | 3-Cl-C₆H₄- | H | 2-CH₃ | C₆H₅- | C₆H₅- |
| 48 | 2,3-Cl₂-C₆H₃- | H | 2-CH₃ | 4-CH₃-C₆H₄- | 4-CH₃-C₆H₄- |
| 49 | 2,3-Cl₂-C₆H₃- | H | 2-CH₃ | 2,5-(CH₃)₂-C₆H₃- | C₆H₅- |
| 50 | 4-Cl-C₆H₄- | H | 2-CH₃ | 4-CH₃O-C₆H₄- | C₆H₅- |
| 51 | 4-Cl-C₆H₄- | H | 2-CH₃ | 4-CH₃-C₆H₄- | C₆H₅- |

TABLE 2-continued

| Compound No. | Ar | R | Substituted Position R¹ | R² | R³ |
|---|---|---|---|---|---|
| 52 | 2-Cl-phenyl | H | 2-OCH$_3$ | phenyl | —CH$_2$-phenyl |
| 53 | 2-Cl-phenyl | H | 2-OCH$_3$ | phenyl | phenyl |
| 54 | 4-Cl-phenyl | H | 2-OCH$_3$ | 4-CH$_3$-phenyl | 4-CH$_3$-phenyl |
| 55 | 4-Cl-phenyl | H | 3-CH$_3$ | phenyl | phenyl |
| 56 | 2-Cl-phenyl | H | 3-OCH$_3$ | phenyl | phenyl |
| 57 | phenyl | —CH$_3$ | 2-CH$_3$ | phenyl | —C$_2$H$_5$ |
| 58 | phenyl | —CH$_3$ | 2-CH$_3$ | phenyl | phenyl |
| 59 | phenyl | —CH$_3$ | 2-CH$_3$ | 4-CH$_3$-phenyl | 4-CH$_3$-phenyl |
| 60 | phenyl | —CH$_3$ | 2-CH$_3$ | 2,4-di-CH$_3$-phenyl | phenyl |
| 61 | phenyl | —CH$_3$ | 2-CH$_3$ | 4-OCH$_3$-phenyl | phenyl |

TABLE 2-continued

| Compound No. | Ar | R | Substituted Position R¹ | R² | R³ |
|---|---|---|---|---|---|
| 62 | phenyl | —CH$_3$ | 2-CH$_3$ | 2,4-dimethylphenyl | phenyl |
| 63 | phenyl | —CH$_3$ | 2-CH$_3$ | 4-CN-phenyl | phenyl |
| 64 | phenyl | —CH$_3$ | 2-OCH$_3$ | phenyl | phenyl |
| 65 | phenyl | —CH$_3$ | 2-OCH$_3$ | 4-OCH$_3$-phenyl | 4-OCH$_3$-phenyl |
| 66 | phenyl | —CH$_3$ | 2-OCH$_3$ | 4-Cl-phenyl | phenyl |
| 67 | phenyl | —CH$_3$ | 2-OCH$_3$ | 4-COCH$_3$-phenyl | phenyl |
| 68 | phenyl | —CH$_3$ | 3-CH$_3$ | phenyl | phenyl |
| 69 | phenyl | —CH$_3$ | 3-OCH$_3$ | 4-OCH$_3$-phenyl | 4-OCH$_3$-phenyl |
| 70 | 4-CH$_3$-phenyl | —CH$_3$ | 2-CH$_3$ | phenyl | phenyl |
| 71 | 4-CH$_3$-phenyl | —CH$_3$ | 2-CH$_3$ | 4-OCH$_3$-phenyl | phenyl |

TABLE 2-continued

Structure:
Ar\\C=CH—[phenyl with R¹]—N(R²)(R³)
R/

Substituted Position: 2,3 on phenyl ring bearing R¹

| Compound No. | Ar | R | R¹ | R² | R³ |
|---|---|---|---|---|---|
| 72 | 2-CH₃, 5-OCH₃-phenyl (CH₃ and OCH₃ substituted phenyl) | —CH₃ | 2-CH₃ | 4-CH₃-phenyl | 4-CH₃-phenyl |
| 73 | phenyl | phenyl | 2-CH₃ | phenyl | —CH₂-phenyl |
| 74 | phenyl | phenyl | 2-CH₃ | phenyl | phenyl |
| 75 | phenyl | phenyl | 2-CH₃ | 4-CH₃-phenyl | 4-CH₃-phenyl |
| 76 | phenyl | phenyl | 2-CH₃ | 4-OCH₃-phenyl | phenyl |
| 77 | phenyl | phenyl | 2-CH₃ | 2,4-di-CH₃-phenyl | phenyl |
| 78 | phenyl | phenyl | 2-CH₃ | 4-CH₃-phenyl | phenyl |
| 79 | phenyl | phenyl | 2-CH₃ | 4-Cl-phenyl | phenyl |
| 80 | phenyl | phenyl | 2-CH₃ | 4-NO₂-phenyl | phenyl |
| 81 | phenyl | phenyl | 2-OCH₃ | phenyl | phenyl |

TABLE 2-continued

Ar\
\|\
C=CH—〈Ar'〉—NR²R³\
\|         \|\
R         R¹

Substituted Position:
positions 2 and 3 on the central ring.

| Compound No. | Ar | R | R¹ | R² | R³ |
|---|---|---|---|---|---|
| 82 | Ph— | Ph— | 2-OCH₃ | 4-CH₃-C₆H₄— | 4-CH₃-C₆H₄— |
| 83 | Ph— | Ph— | 2-OCH₃ | 4-CH₃-C₆H₄— | Ph— |
| 84 | Ph— | Ph— | 2-OCH₃ | 4-Cl-C₆H₄— | Ph— |
| 85 | Ph— | Ph— | 2-OCH₃ | 4-(CO₂C₂H₅)-C₆H₄— | Ph— |
| 86 | Ph— | Ph— | 3-CH₃ | Ph— | Ph— |
| 87 | Ph-CH=CH— | H | 2-CH₃ | Ph— | —C₂H₅ |
| 88 | Ph-CH=CH— | H | 2-CH₃ | Ph— | Ph— |
| 89 | Ph-CH=CH— | H | 2-CH₃ | 4-CH₃-C₆H₄— | 4-CH₃-C₆H₄— |
| 90 | Ph-CH=CH— | H | 2-CH₃ | 2,4-(CH₃)₂-C₆H₃— | Ph— |
| 91 | Ph-CH=CH— | H | 2-CH₃ | 4-CH₃-C₆H₄— | Ph— |

TABLE 2-continued

Structure:

Ar\
 \
  C=CH—[phenyl with R¹]—N(R²)(R³)
 /
R

Substituted Position: 2, 3 on phenyl ring

| Compound No. | Ar | R | R¹ | R² | R³ |
|---|---|---|---|---|---|
| 92 | phenyl-CH=CH— | H | 2-CH₃ | 4-Cl-phenyl | phenyl |
| 93 | phenyl-CH=CH— | H | 2-OCH₃ | phenyl | phenyl |
| 94 | phenyl-CH=CH— | H | 2-OCH₃ | 4-CH₃-phenyl | 4-CH₃-phenyl |
| 95 | phenyl-CH=CH— | H | 3-CH₃ | phenyl | phenyl |

Of the styrene derivatives of the previously described formula (I), thiophene-type derivatives of the following formula (Ib), in which A is

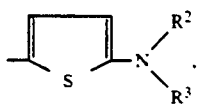

can be synthesized by reacting a phenyl derivative of formula (IIb) with an aldehyde compound of formula (IIIb) under the same conditions, using the same reaction solvents and catalysts as in the case of the stilbene-type derivatives of the formula (Ia).

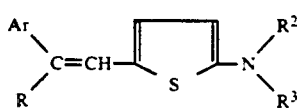
(Ib)

wherein Ar, R, $R^2$ and $R^3$ are respectively the same as those defined in the stilbene-type derivatives of the previously described formula (Ia). That is, Ar represents an unsubstituted or substituted phenyl group or an unsubstituted or substituted styryl group. R represents hydrogen, a lower alkyl group or an unsubstituted or substituted phenyl group. $R^2$ and $R^3$ each represent a lower alkyl group, a lower aralkyl group or an unsubstituted or substituted phenyl group.

(IIb)

wherein Ar and R are respectively the same as those defined in formula (Ib) and Y represents a triphenylphosphonium group of the formula

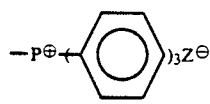

in which $Z^\ominus$ represents a halogen, or a dialkylphosphorous group of the formula —$PO(OR^4)_2$ in which $R^4$ represents a lower alkyl group.

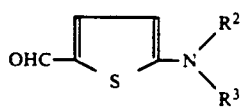
(IIIb)

wherein $R^2$ and $R^3$ are respectively the same as those defined in formula (Ib).

Furthermore, the preferable substituents of the phenyl group in Ar, R, $R^2$ and $R^3$ are the same as those of the stilbene-type derivatives of the previously described formula (Ia).

Preparation of the thiophene-type derivatives of the formula (Ib) will now be explained in detail by referring to the following examples:

SYNTHESIS EXAMPLE 8

SYNTHESIS EXAMPLES 9 THROUGH 12

Further thiophene-type derivatives as listed in Table 3 were prepared under the same procedure as in Synthesis Example 8.

TABLE 3

| Example No. | Thiophene Type Derivatives | Melting Point (°C.) | Elemental Analysis Found/Calculated | | |
|---|---|---|---|---|---|
| | | | % C | % H | % N |
| 9 | Ph—CH=CH—[thiophene]—N(Ph-CH$_3$)$_2$ | 142.0–143.0 | 81.79/ 81.84 | 6.08/ 6.09 | 3.60/ 3.67 |
| 10 | (o-CH$_3$)Ph—CH=CH—[thiophene]—N(Ph-CH$_3$)$_2$ | 93.5–95.0 | 81.95/ 81.97 | 6.40/ 6.38 | 3.49/ 3.54 |
| 11 | Ph—C(CH$_3$)=CH—[thiophene]—N(Ph-CH$_3$)$_2$ | Oily Material | 81.82/ 81.97 | 6.22/ 6.38 | 3.37/ 3.54 |
| 12 | Ph—CH=CH—CH=CH—[thiophene]—N(Ph-CH$_3$)$_2$ | 175.5–176.5 | 82.41/ 82.50 | 6.40/ 6.19 | 3.49/ 3.44 |

30.4 g (0.1 mol) of diethyl 1,1-diphenylmethylphosphonate and 30.7 g (0.1 mol) of 2-N,N-ditolylamino-5-thiophene aldehyde were dissolved in 100 ml of N,N-dimethylformamide. To this mixture, 16.8 g (0.15 mol) of potassium-tert-butoxide was added with the temperature of the reaction mixture maintained in the range of from 25° C. to 35° C. After the addition of the potassium-tert-butoxide, the reaction mixture was stirred at room temperature for 6 hours and was then diluted with 200 ml of water. Powder separated from the reaction mixture was filtered, washed with water and dried, whereby light yellow powder was obtained. The yield was 42.1 g (92%) and the melting point was 155.5~157° C. The thus obtained light yellow powder was recrystallized from a mixed solvent of ethyl acetate and ethanol, whereby pure 2-N,N-ditolylamino-5-(β-phenylstyryl) thiophene was obtained. The melting point of the product was 157.0~158.0° C.

Figure 2:
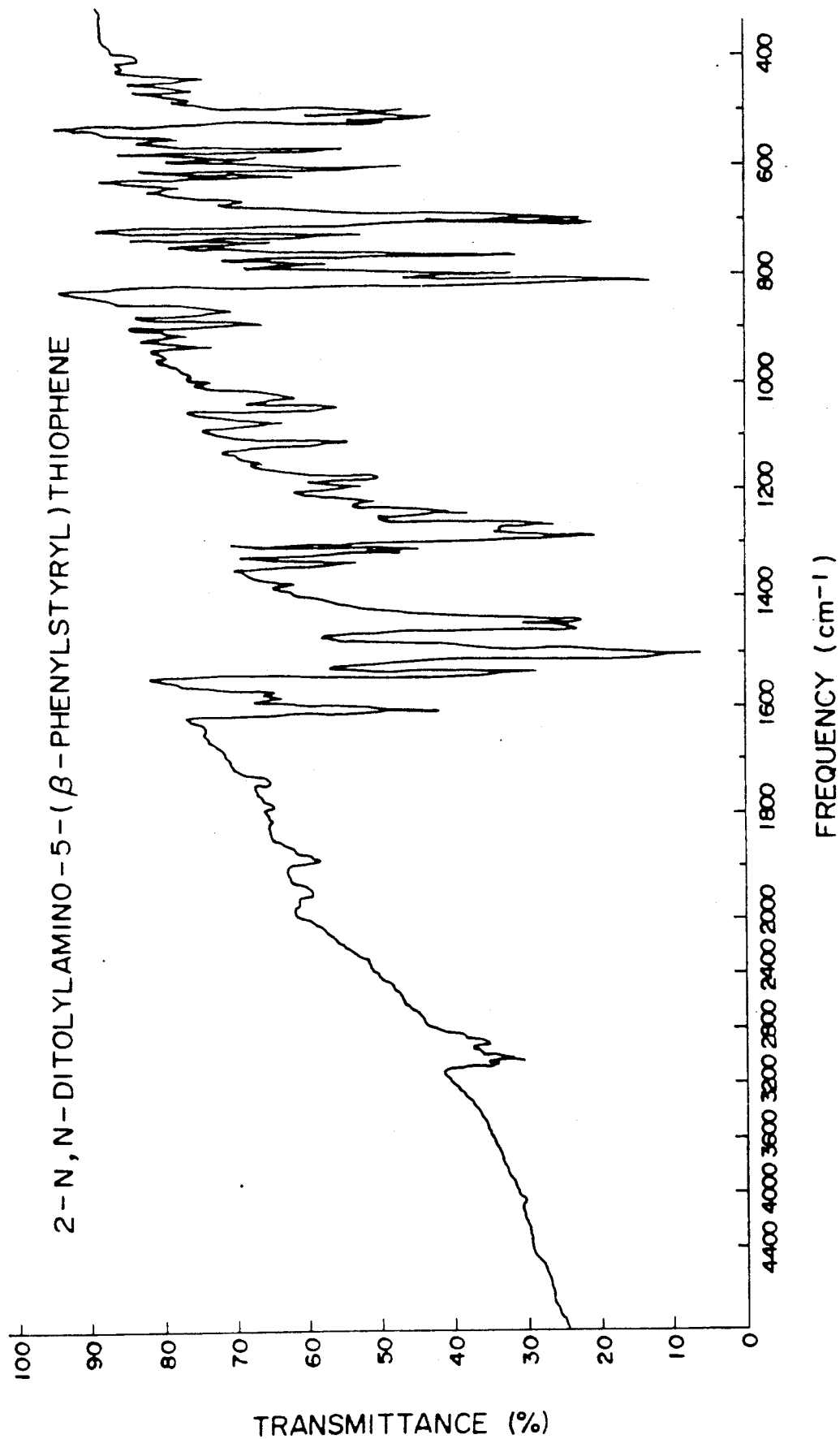
FIG. 2 is an infrared spectrum of 2-N,N-ditolylamino-5-(β-8-phenylstyryl) thiophene.

An infrared spectrum of the 2-N,N-ditolylamino-5-(β-phenylstyryl) thiophene, taken by use of a KBr pellet, is shown in FIG. 2.

The results of the elemental analysis of the thus obtained 2-N,N-ditolylamino-5-(β-phenylstyryl) thiophene were were as follows:

| | % C | % H | % N | % S |
|---|---|---|---|---|
| Found | 83.82 | 5.92 | 3.07 | 6.99 |
| Calculated | 83.98 | 5.96 | 3.06 | 7.01 |

The above calculation was based on the formula for 2-N,N-ditolylamino-5-(8-phenylstyryl) thiophene of C$_{32}$H$_{27}$NS.

SYNTHESIS EXAMPLE 13

42.3 g (0.1 mol) of 4-chlorobenzyltriphenylphosphonium chloride and 30.7 g (0.1 mol) of 2-N,N-dimethylamino-5-thiophene aldehyde were dissolved in 100 ml of N,N-dimethylformamide. To this mixture, 16.8 g (0.15 mol) of potassium-tert-butoxide was added with the temperature of the reaction mixture maintained in the range of from 25° C. to 35° C. After the addition of the potassium-tert-butoxide, the reaction mixture was stirred at room temperature for 5 hours and was then diluted with 200 ml of water. Powder separated from the reaction mixture was filtered, washed with water and dried, whereby light yellow powder was obtained. The yield was 40.3 g (97%) and the melting point of the product was 142.0~143.5° C.

Upon recrystallization of the powder from a mixed solvent of toluene and n-hexane in the presence of a small amount of iodine, 2-N,N-ditolylamino-5,4'-chlorostyrylthiophene precipitated as light yellow needle-like crystal. The yield was 38.2 g (91.8%). The melting point of the product was 143.0~143.7° C.

The results of the elemental analysis of the thus obtained 2-N,N-ditolylamino-5,4'-chlorostyrylthiophene were as follows:

| | % C | % H | % N | % Cl |
|---|---|---|---|---|
| Found | 75.07 | 5.80 | 3.24 | 8.43 |
| Calculated | 75.07 | 5.33 | 3.37 | 8.52 |

The above calculation was based on the formula for 2-N,N-ditolylamino-5,4'-chlorostyrylthiophene of C$_{26}$H$_{22}$NSCl.

In addition to the thiophene-type derivatives described in Synthesis Examples 8 through 13, other thiophene-type derivatives of the formula (Ib), that is,

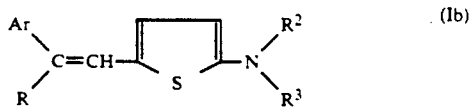

which are also suitable for use in the present invention, are listed in the following Table 4.

TABLE 4

Structure: Ar(R)C=CH—[thiophene]—N(R²)(R³)

| Compound No. | Ar | R | R² | R³ |
|---|---|---|---|---|
| 96 | phenyl | H | phenyl | —CH₃ |
| 97 | phenyl | H | phenyl | phenyl |
| 98 | phenyl | H | 4-CH₃-phenyl | 4-CH₃-phenyl |
| 99 | phenyl | H | 4-CH₃-phenyl | phenyl |
| 100 | phenyl | H | 3,4-(CH₃)₂-phenyl | phenyl |
| 101 | 2-CH₃-phenyl | H | phenyl | —CH₂-phenyl |
| 102 | 4-CH₃-phenyl | H | phenyl | phenyl |
| 103 | 2,3-(CH₃)₂-phenyl | H | 4-CH₃-phenyl | 4-CH₃-phenyl |
| 104 | 4-CH₃-phenyl | H | 4-OCH₃-phenyl | 4-OCH₃-phenyl |
| 105 | 4-CH₃-phenyl | H | 4-Cl-phenyl | phenyl |

TABLE 4-continued
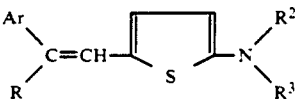
| Compound No. | Ar | R | R² | R³ |
|---|---|---|---|---|
| 106 | 4-CH₃O-C₆H₄- | H | C₆H₅- | —C₂H₅ |
| 107 | 4-CH₃O-C₆H₄- | H | C₆H₅- | C₆H₅- |
| 108 | 4-CH₃O-C₆H₄- | H | 4-CH₃-C₆H₄- | 4-CH₃-C₆H₄- |
| 109 | 2-CH₃O-C₆H₄- | H | 4-CH₃-C₆H₄- | C₆H₅- |
| 110 | 2-CH₃O-C₆H₄- | H | 4-CN-C₆H₄- | C₆H₅- |
| 111 | 4-Cl-C₆H₄- | H | C₆H₅- | C₆H₅- |
| 112 | 4-Cl-C₆H₄- | H | 4-CH₃-C₆H₄- | 4-CH₃-C₆H₄- |
| 113 | 2-Cl-C₆H₄- | H | 4-CH₃O-C₆H₄- | 4-CH₃O-C₆H₄- |
| 114 | 4-Cl-C₆H₄- | H | 4-CH₃O-C₆H₄- | C₆H₅- |
| 115 | 4-Cl-C₆H₄- | H | 4-Cl-C₆H₄- | C₆H₅- |
| 116 | C₆H₅- | —CH₃ | C₆H₅- | —C₂H₅ |

TABLE 4-continued
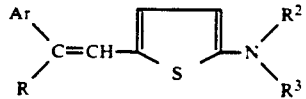
| Compound No. | Ar | R | R² | R³ |
|---|---|---|---|---|
| 117 | Ph- | —CH₃ | -Ph | -Ph |
| 118 | Ph- | —CH₃ | -C₆H₄-OCH₃ | -C₆H₄-OCH₃ |
| 119 | Ph- | —CH₃ | -C₆H₄-CH₃ | -C₆H₄-CH₃ |
| 120 | Ph- | —CH₃ | -C₆H₄-CH₃ | -Ph |
| 121 | Ph- | —CH₃ | -C₆H₄-CN | -Ph |
| 122 | Ph- | —CH₃ | -C₆H₄-COCH₃ | -Ph |
| 123 | CH₃-C₆H₄- | —CH₃ | -Ph | -Ph |
| 124 | Ph- | -Ph | -Ph | -CH₂-Ph |
| 125 | Ph- | -Ph | -Ph | -Ph |
| 126 | Ph- | -Ph | -C₆H₄-CH₃ | -C₆H₄-CH₃ |
| 127 | Ph- | -Ph | -C₆H₄-OCH₃ | -C₆H₄-OCH₃ |
| 128 | Ph- | -Ph | -C₆H₄-Cl | -Ph |

TABLE 4-continued

| Compound No. | Ar | R | R² | R³ |
|---|---|---|---|---|
| 129 | C₆H₅ | C₆H₅ | 4-(COOC₂H₅)C₆H₄ | C₆H₅ |
| 130 | C₆H₅ | C₆H₅ | 2,4-(CH₃)₂C₆H₃ | C₆H₅ |
| 131 | C₆H₅—CH=CH— | H | C₆H₅ | C₆H₅ |
| 132 | C₆H₅—CH=CH— | H | 4-CH₃C₆H₄ | 4-CH₃C₆H₄ |
| 133 | C₆H₅—CH=CH— | H | 4-OCH₃C₆H₄ | 4-OCH₃C₆H₄ |
| 134 | C₆H₅—CH=CH— | H | 4-CH₃C₆H₄ | C₆H₅ |
| 135 | C₆H₅—CH=CH— | H | 4-ClC₆H₄ | C₆H₅ |
| 136 | 4-CH₃C₆H₄—CH=CH— | H | C₆H₅ | C₆H₅ |
| 137 | 4-CH₃C₆H₄—CH=CH— | H | 4-CH₃C₆H₄ | 4-CH₃C₆H₄ |
| 138 | 3-CH₃C₆H₄ | H | 4-CH₃C₆H₄ | 4-CH₃C₆H₄ |
| 139 | 4-CH₃C₆H₄ | H | 4-CH₃C₆H₄ | 4-CH₃C₆H₄ |
| 140 | 2-ClC₆H₄ | H | 4-CH₃C₆H₄ | 4-CH₃C₆H₄ |

TABLE 4-continued

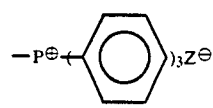

| Compound No. | Ar | R | R² | R³ |
|---|---|---|---|---|
| 141 | 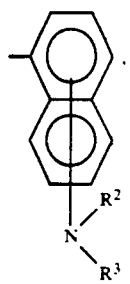 Cl | H | 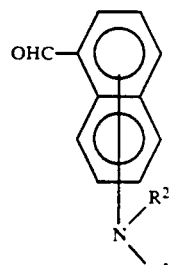 —CH₃ | —CH₃ |

Of the styrene derivatives of the previously described formula (I), naphthalene-type styrene derivatives of the following formula (Ic), in which A is

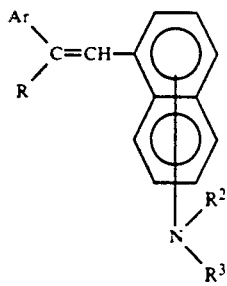

can be synthesized by reacting a phenyl derivative of formula (IIc) with an aldehyde compound of formula (IIIc) under the same conditions, using the same reaction solvents and catalysts as in the case of the stilbene-type derivatives of the formula (Ia).

(Ic)

wherein Ar, R, R² and R³ are respectively the same as those defined in the stilbene-type derivatives of the previously described formula (Ia). That is, Ar represents an unsubstituted or substituted phenyl group or an unsubstituted or substituted styryl group, R represents hydrogen, a lower alkyl group or an unsubstituted or substituted phenyl group, R² and R³ each represent a lower alkyl group, a lower aralkyl group or an unsubstituted or substituted phenyl group.

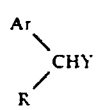 (IIc)

wherein Ar and R are respectively the same as those defined in the formula (Ic) and Y represents a triphenyl-phosphonium group of the formula $$-P^{\oplus}\!\!-\!\!\bigcirc\!\!)_3 Z^{\ominus}$$

in which $Z^{\ominus}$ represents a halogen or a dialkylphosphorous group of the formula $-PO(OR^4)_2$ in which $R^4$ represents a lower alkyl group.

(IIIb)

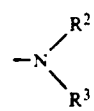

wherein R² and R³ are respectively the same as those defined in formula (Ic).

In the above formula (Ic), the substitution position of $$-N\!\!\begin{array}{c}R^2\\R^3\end{array}$$

is preferably 4- or 5-position of the naphthalene group. The preferable substituents of the phenyl group in Ar and R¹ are, for example, an alkyl group such as methyl, ethyl, propyl and butyl; an alkoxy group such as methoxy, ethoxy, propoxy and butoxy; a phenoxy group, a benzyloxy group; halogen such as chlorine and bromine; and the preferable substituents of the phenyl group in R² and R³ are, for example, an alkyl group such as methyl, ethyl, propyl and butyl; an alkoxy group such as methoxy, ethoxy, propoxy and butoxty; a thioalkoxy group such as thiomethoxy and thioethoxy; a thiophenyl group; halogen such as chlorine and bromine; a dialkylamino group such as dimethylamino, diethylamino, dipropylamino, N-methyl-N-ethylamino; a hydroxy group, a carboxy group and ester groups thereof; an acyl group; an aryloxy group such as a phenoxy, an aralkyloxy group such as benzyloxy; a trifluoromethyl group, a nitro group and a cyano group.

Preparation of the naphthalene-type derivatives of the formula (Ic) will now be explained in detail by referring to the following examples:

SYNTHESIS EXAMPLE 14

30.4 g (0.1 mol) of diethyl 1,1-diphenylmethylphosphonate and 32.3 g (0.1 mol) of 4-N,N-diphenylaminonaphthaldehyde were dissolved in 100 ml of N,N-dimethylformamide. To this mixture, 16.8 g (0.15 mol) of potassium-tert-butoxide was added with the temperature of the reaction mixture maintained in the range of from 25° C. to 35° C. After the addition of the potassium-tert-butoxide, the reaction mixture was stirred at room temperature for 8 hours and was then diluted with 200 ml of water. Powder separated from the reaction mixture was filtered, washed with water and dried, whereby light yellow powder was obtained. The yield was 38.9 g (82%). The thus obtained light yellow powder was recrystallized from a mixed solvent of methyl acetate and ethanol and was then washed with methanol, whereby pure 1-N,N-diphenylamino-4-(8-phenylstyryl) naphthalene was obtained.

The results of the elemental analysis of the thus obtained 1-N,N-diphenylamino-4-(8-phenylstyryl) naphthalene were as follows:

|  | % C | % H | % N |
|---|---|---|---|
| Found | 91.23 | 5.75 | 3.01 |
| Calculated | 91.28 | 5.76 | 2.96 |

The above calculation was based on the formula for of 1-N,N-diphenylamino-4-(8-phenylstyryl)naphthalene of $C_{36}H_{27}N$.

Figure 3:
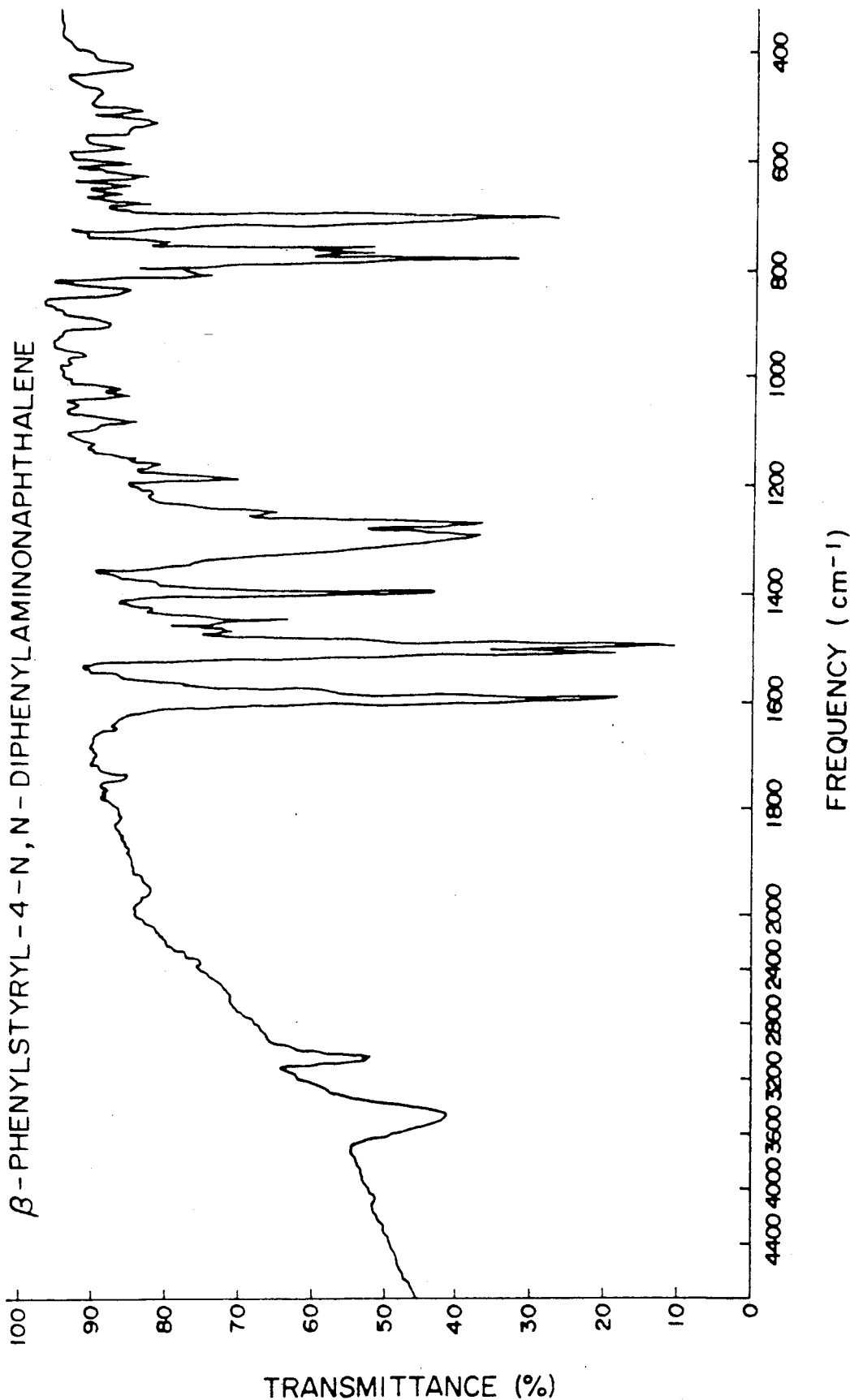
FIG. 3 is an infrared spectrum of β-phenylstyryl-4-N, N-diphenylaminonaphthalene.

An infrared spectrum of the 1-N,N-diphenylamino-4-(β-phenylstyryl) naphthalene (or 8-phenylstyryl-4-N,N-diphenylaminonaphthalene), taken by use of a KBr pellet, is shown in FIG. 3.

SYNTHESIS EXAMPLES 15 THROUGH 20

Further naphthalene-type derivatives as listed in Table 5 were prepared by the same method as in Synthesis Example 1.

TABLE 5

| Example No. | Naphthalene Type Derivatives | Melting Point (°C.) | Elemental Analysis Found/Calculated | | |
|---|---|---|---|---|---|
| | | | % C | % H | % N |
| 15 | | 148.0–149.0 | 90.62/ 90.63 | 5.58/ 5.84 | 3.45/ 3.52 |
| 16 | | 157.5–158.5 | 91.37/ 91.28 | 5.64/ 5.76 | 3.07/ 2.96 |
| 17 | | 103.5–105.0 | 90.32/ 90.46 | 6.00/ 6.14 | 3.41/ 3.40 |
| 18 | | 153.0–155.0 | 90.62/ 90.73 | 6.01/ 5.96 | 3.30/ 3.31 |
| 19 | | 143.5–145.0 | 87.01/ 87.08 | 5.85/ 5.91 | 3.29/ 3.28 |

TABLE 5-continued

| Example No. | Naphthalene Type Derivatives | Melting Point (°C.) | Elemental Analysis Found/Calculated | | |
|---|---|---|---|---|---|
| | | | % C | % H | % N |
| 20 | (structure: Ph-CH=CH(CH₃)-naphthalene-N(Ph)₂) | 157.5~158.5 | 90.37/90.46 | 6.10/6.14 | 3.42/3.40 |

SYNTHESIS EXAMPLE 21

42.3 g (0.1 mol) of 4-chlorobenzyltriphenylphosphonium chloride and 32.3 g (0.1 mol) of 4-N,N-diphenylaminonaphthaldehyde were dissolved in 100 ml of N,N-dimethylformamide. To this mixture, 16.8 g (0.15 mol) of potassium-tert-butoxide was added with the temperature of the reaction mixture maintained in the range of from 25° C. to 35° C. After the addition of the potassium-tert-butoxide, the reaction mixture was stirred at room temperature for 5 hours and was then diluted with 300 ml of water. Powder separated from the reaction mixture was filtered, washed with water and dried, whereby light yellow powder was obtained. The yield was 39.3 g (91%) and the melting point of the product was 126.0~127.5° C.

Upon recrystallization of the powder from a mixed solvent of toluene and n-hexane in the presence of a small amount of iodine, 1-N,N-diphenylamino-4-(4-chlorostyryl) naphthalene precipitated as light yellow needle-like crystal. The yield was 34.8 g (80.7%). The melting point of the product was 127.0~128.5° C.

The results of the elemental analysis of the thus obtained 1-N,N-diphenylamino-4-(4-chlorostyryl) naphthalene were as follows:

| | % C | % H | % N | % C |
|---|---|---|---|---|
| Found | 83.57 | 5.11 | 5.25 | 8.05 |
| Calculated | 83.42 | 5.13 | 5.24 | 8.21 |

The above calculation was based on the formula for 1-N,N-diphenylamino-4-(4-chlorostyryl) naphthalene of $C_{30}H_{22}NCl$.

In addition to the naphthalene-type derivatives described in Synthesis Examples 14 through 21, other naphthalene-type derivatives of the formula (Ic), that is,

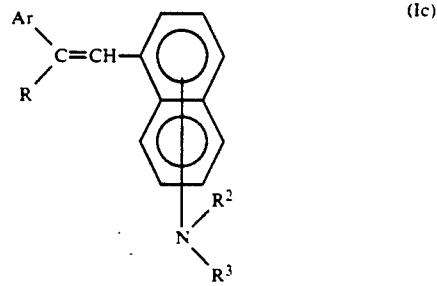

(Ic)

which are also suitable for use in the present invention, are listed in the following Table 6.

TABLE 6

(structure showing Ar\C=CH- connected to naphthalene with positions 4 and 5, and N with R² and R³)

| Compound No. | Ar | R | Substituted Position -N(R²)(R³) | R² | R³ |
|---|---|---|---|---|---|
| 142 | phenyl | H | 4 | phenyl | —CH₃ |

TABLE 6-continued
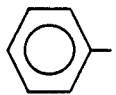
| Compound No. | Ar | R | Substituted Position −N(R²)(R³) | R² | R³ |
|---|---|---|---|---|---|
| 143 | Ph | H | 4 | Ph | Ph |
| 144 | Ph | H | 4 | 4-CH₃-C₆H₄ | Ph |
| 145 | Ph | H | 4 | 4-CH₃-C₆H₄ | 4-CH₃-C₆H₄ |
| 146 | Ph | H | 4 | 4-Cl-C₆H₄ | Ph |
| 147 | Ph | —CH₃ | 4 | Ph | —C₂H₅ |
| 148 | Ph | —CH₃ | 4 | Ph | —CH₂—Ph |
| 149 | Ph | —CH₃ | 4 | Ph | Ph |
| 150 | Ph | —CH₃ | 5 | Ph | Ph |
| 151 | Ph | —CH₃ | 4 | 4-CH₃-C₆H₄ | 4-CH₃-C₆H₄ |
| 152 | Ph | —CH₃ | 4 | 4-OCH₃-C₆H₄ | Ph |

TABLE 6-continued

| Compound No. | Ar | R | Substituted Position -N(R²)(R³) | R² | R³ |
|---|---|---|---|---|---|
| 153 | Ph | —CH₃ | 4 | 2,4-dimethylphenyl | Ph |
| 154 | Ph | —CH₃ | 4 | 4-Cl-phenyl | Ph |
| 155 | Ph | —CH₃ | 4 | 4-CN-phenyl | Ph |
| 156 | Ph | Ph | 4 | Ph | —CH₃ |
| 157 | Ph | Ph | 4 | Ph | —C₂H₅ |
| 158 | Ph | Ph | 4 | Ph | —CH₂—Ph |
| 159 | Ph | Ph | 4 | Ph | Ph |
| 160 | Ph | Ph | 4 | 4-OCH₃-phenyl | 4-OCH₃-phenyl |
| 161 | Ph | Ph | 4 | 4-CH₃-phenyl | 4-CH₃-phenyl |
| 162 | Ph | Ph | 4 | 4-OCH₃-phenyl | Ph |

TABLE 6-continued
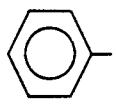
| Compound No. | Ar | R | Substituted Position $-N\begin{matrix}R^2\\R^3\end{matrix}$ | $R^2$ | $R^3$ |
|---|---|---|---|---|---|
| 163 | 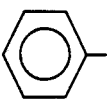 | 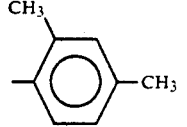 | 4 | 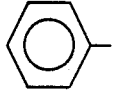 (2,4-diCH₃) | 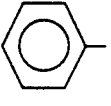 |
| 164 | 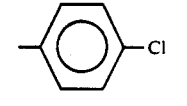 | 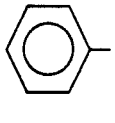 | 4 | 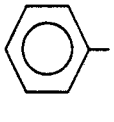 Cl | 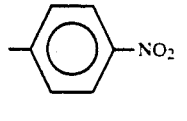 |
| 165 | 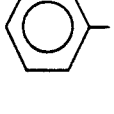 | 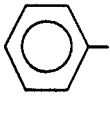 | 4 | 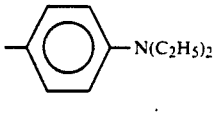 NO₂ | 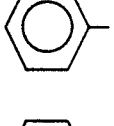 |
| 166 | 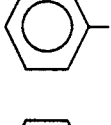 | 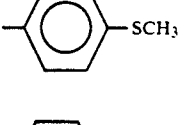 | 4 | 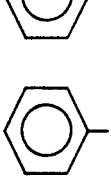 N(C₂H₅)₂ |  |
| 167 |  |  | 4 |  SCH₃ |  |
| 168 | 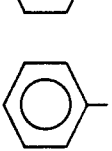 | 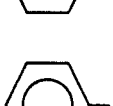 | 4 | 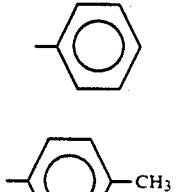 COCH₃ |  |
| 169 | 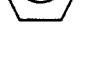 | 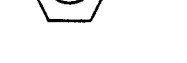 | 5 | phenyl | —C₂H₅ |
| 170 | phenyl | phenyl | 5 | phenyl | phenyl |
| 171 | phenyl | phenyl | 5 | 4-CH₃-phenyl | 4-CH₃-phenyl |

TABLE 6-continued
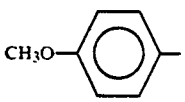
| Compound No. | Ar | R | Substituted Position -N(R²)(R³) | R² | R³ |
|---|---|---|---|---|---|
| 172 | 4-CH₃O-C₆H₄- | H | 4 | C₆H₅- | —C₂H₅ |
| 173 | 2-CH₃O-C₆H₄- | H | 4 | C₆H₅- | —CH₂-C₆H₅ |
| 174 | 4-CH₃O-C₆H₄- | H | 4 | C₆H₅- | C₆H₅- |
| 175 | 3-CH₃O-C₆H₄- | H | 4 | C₆H₅- | C₆H₅- |
| 176 | 2-CH₃O-C₆H₄- | H | 4 | C₆H₅- | C₆H₅- |
| 177 | 4-CH₃O-C₆H₄- | H | 4 | 4-CH₃O-C₆H₄- | C₆H₅- |
| 178 | 4-CH₃O-C₆H₄- | H | 4 | 4-CH₃-C₆H₄- | C₆H₅- |
| 179 | 2-CH₃O-C₆H₄- | H | 4 | 4-Cl-C₆H₄- | C₆H₅- |
| 180 | 4-CH₃-C₆H₄- | H | 4 | C₆H₅- | —C₂H₅ |

TABLE 6-continued

| Compound No. | Ar | R | Substituted Position -N(R²)(R³) | R² | R³ |
|---|---|---|---|---|---|
| 181 | 4-CH₃-C₆H₄- | H | 4 | 4-OCH₃-C₆H₄- | —C₂H₅ |
| 182 | 2-CH₃-C₆H₄- | H | 4 | C₆H₅- | C₆H₅- |
| 183 | 3-CH₃-C₆H₄- | H | 4 | 4-CH₃-C₆H₄- | 4-CH₃-C₆H₄- |
| 184 | 4-CH₃-C₆H₄- | H | 4 | 4-CH₃-C₆H₄- | 4-CH₃-C₆H₄- |
| 185 | 4-CH₃-C₆H₄- | H | 4 | 4-OCH₃-C₆H₄- | 4-OCH₃-C₆H₄- |
| 186 | 4-Cl-C₆H₄- | H | 4 | C₆H₅- | —C₂H₅ |
| 187 | 4-Cl-C₆H₄- | H | 4 | C₆H₅- | C₆H₅- |
| 188 | 3-Cl-C₆H₄- | H | 4 | C₆H₅- | C₆H₅- |
| 189 | 2-Cl-C₆H₄- | H | 4 | C₆H₅- | C₆H₅- |

TABLE 6-continued

Structure: Ar(R)C=CH-naphthyl with NR²R³ substituent at position 4 or 5

| Compound No. | Ar | R | Substituted Position -NR²R³ | R² | R³ |
|---|---|---|---|---|---|
| 190 | 2-Cl-phenyl | H | 4 | 4-CH₃-phenyl | 4-CH₃-phenyl |
| 191 | 4-Cl-phenyl | H | 4 | 4-OCH₃-phenyl | phenyl |
| 192 | 4-Cl-phenyl | H | 4 | 4-CH₃-phenyl | phenyl |
| 193 | 4-Cl-phenyl | H | 5 | phenyl | phenyl |
| 194 | phenyl-CH=CH- | H | 4 | phenyl | —C₂H₅ |
| 195 | phenyl-CH=CH- | H | 4 | phenyl | phenyl |
| 196 | phenyl-CH=CH- | H | 5 | phenyl | phenyl |
| 197 | phenyl-CH=CH- | H | 4 | 4-CH₃-phenyl | 4-CH₃-phenyl |
| 198 | phenyl-CH=CH- | H | 4 | 4-OCH₃-phenyl | phenyl |

TABLE 6-continued

[Structure: Ar\C=CH-naphthyl(4,5)-N(R²)(R³), with R on the C]

Substituted Position: -N(R²)(R³)

| Compound No. | Ar | R | Substituted Position | R² | R³ |
|---|---|---|---|---|---|
| 199 | phenyl-CH=CH- | H | 4 | 3,4-dimethylphenyl | phenyl |
| 200 | phenyl-CH=CH- | H | 4 | 4-chlorophenyl | phenyl |
| 201 | phenyl-CH=CH- | H | 4 | 4-cyanophenyl | phenyl |
| 202 | 4-CH₃-phenyl-CH=CH- | H | 4 | phenyl | -C₂H₅ |
| 203 | 2-CH₃-phenyl-CH=CH- | H | 4 | phenyl | phenyl |
| 204 | 4-CH₃-phenyl-CH=CH- | H | 4 | 4-methylphenyl | 4-methylphenyl |
| 205 | 4-CH₃-phenyl-CH=CH- | H | 4 | 4-methoxyphenyl | phenyl |
| 206 | 4-CH₃-phenyl-CH=CH- | H | 4 | 4-methoxyphenyl | phenyl |

In the electrophotographic photoconductor according to the present invention, at least one styrene derivative of the previously described formula (I) is contained in the photosensitive layer. Those styrene derivatives can be employed in different ways, for example, as shown in FIG. 4, FIG. 5 and FIG. 6.

Figure 4:
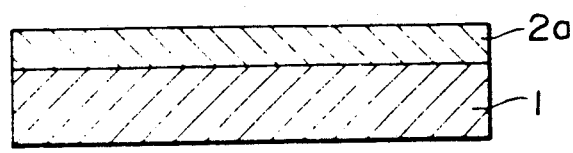
FIG. 4 is an enlarged schematic cross-sectional view of an embodiment of an electrophotographic photoconductor according to the present invention.

In the photoconductor shown in FIG. 4, a photosensitive layer 2a is formed on an electroconductive support material 1, which photosensitive layer 2a comprises a styrene derivative, a sensitizer dye and a binder agent. In this photoconductor, the styrene derivative works as a photoconductor material through which charge carriers are generated and transported. The generation and transportation of charge carrier are necessary for the light decay of the photoconductor. However, the styrene derivative itself scarcely absorbs light in the visible light range. Therefore, it is necessary to add a sensitizer dye which absorbs light in the visible light range in order to form latent electrostatic images on the photoconductor by use of visible light.

Figure 5:
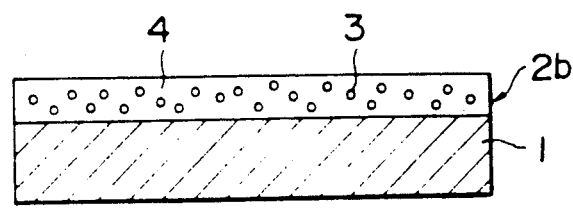
FIG. 5 is an enlarged schematic cross-sectional view of another embodiment of an electrophotographic photoconductor according to the present invention.
Figure 6:
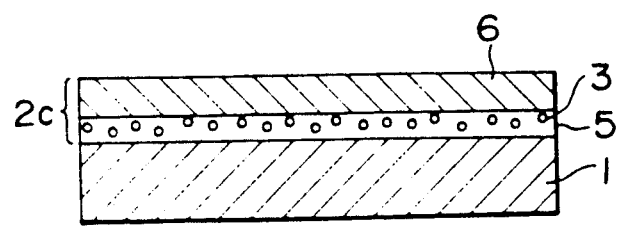
FIG. 6 is an enlarged schematic cross-sectional view of a further embodiment of an electrophotographic photoconductor according to the present invention.

Referring to FIG. 5, there is shown an enlarged crossectional view of another embodiment of an electrophotographic photoconductor according to the present invention.

In the figure, on the electroconductive support material 1, there is formed a photosensitive layer 2b comprising a charge generating material 3 dispersed in a charge transporting medium 4 which comprises a styrene derivative and a binder agent. In this embodiment, the combination of the styrene derivative and the binder agent (or a plasticizer and a binder agent) constitutes the charge transporting medium 4. The charge generating material 3, which is, for example, an inorganic or organic pigment, generates charge carriers. The charge transporting medium 4 mainly serves to accept the charge carriers generated by the charge generating material 3 and to transport those charge carriers.

In this electrophotographic photoconductor, it is a basic requirement that the light-absorption wavelength regions of the charge generating material 3 and the styrene derivative not overlap in the visible light range. This is because, in order that the charge generating material 3 produce charge carriers efficiently, it is necessary that light pass through the charge transporting medium 4 and reach the surface of the charge generating material 3. Since the styrene derivatives of the formula (I) do not substantially absorb light in the visible range, they can work effectively as charge transporting materials when used in combination with the charge generating material 3 which absorbs the light in the visible region and generates charge carriers.

Referring to FIG. 6, there is shown an enlarged crossectional view of a further embodiment of an electrophotographic photoconductor according to the present invention. In the embodiment, there is formed on the electroconductive support material 1 a two-layered photosensitive layer 2c comprising a charge generating layer 5 consisting essentially of the charge generating material 3, and a charge transporting layer 6 containing a styrene derivative of the previously described formula (I).

In this photoconductor, light which has passed through the charge transporting layer 6 reaches the charge generating layer 5, so that charge carriers are generated within the charge generating layer 5 in the region which the light has reached. The charge carriers which are necessary for the light decay for latent electrostatic image formation are generated by the charge generating material 3, accepted and transported by the charge transporting layer 6. In the charge transporting layer 6, the styrene derivative mainly works for transporting charge carriers. The generation and transportation of the charge carriers are performed in the same manner as that in the photoconductor shown in FIG. 5.

When an electrophotographic photoconductor according to the present invention as shown in FIG. 4 is prepared, at least one of the styrene derivatives is dispersed in a binder resin solution, and a sensitizer dye is then added to the mixture, and the thus prepared photosensitive liquid is applied to the electroconductive support material 1 and dried, so that the photosensitive layer 2a is formed on the electroconductive support material 1.

It is preferable that the thickness of the photosensitive layer 2a be in the range of about 3 μm to about 50 μm, more preferably in the range of about 5 μm to about 20 μm. It is preferable that the amount of the styrene derivatives contained in the photosensitive layer 2a be in the range of about 30 wt.% to about 70 wt.% of the total weight of the photosensitive layer 2a, more preferably about 50 wt.%. Further, it is preferable that the amount of the sensitizer dye contained in the photosensitive layer 2a be in the range of about 0.1 wt.% to about 5 wt.% of the total weight of the photosensitive layer 2a, more preferably in the range of about 0.5 wt.% to about 3 wt.%.

As the sensitizer dye, the following can be employed in the present invention: triarylmethane dyes, such as Brilliant Green, Victoria Blue B, Methyl Violet, Crystal Violet and Acid Violet 6B; xanthene dyes, such as Rhodamine B, Rhodamine 6G, Rhodamine G Extra, Eosin S, Erythrosin, Rose Bengale and Fluorescein; thiazine dyes such as Methylene Blue; cyanin dyes such as cyanin; and pyrylium dyes, such as 2,6-diphenyl-4-(N,N-dimethylaminophenyl) thiapyrylium perchlorate and benzopyrylium salt (as described in Japanese Patent Publication 48-25658). These sensitizer dyes can be used alone or in combination.

An electrophotographic photoconductor according to the present invention as shown in FIG. 5 can be prepared, for example, as follows. The charge generating material 3 in the form of small particles is dispersed in a solution of one or more styrene derivatives and a binder agent. The thus prepared dispersion is applied to the electroconductive support material 1 and is then dried, whereby the photosensitive layer 2b is formed on the electroconductive support material 1.

It is preferable that the thickness of the photosensitive layer 2b be in the range of about 3 μm to about 50 μm, more preferably in the range of about 5 μm to about 20 μm. It is preferable that the amount of the styrene derivative contained in the photosensitive layer 2b be in the range of about 10 wt.% to about 95 wt.%, more preferably in the range of about 30 wt.% to about 90 wt.% of the total weight of the photosensitive layer 2b. Further, it is preferable that the amount of the charge generating material 3 contained in the photosensitive layer 2b be in the range of about 0.1 wt.% to about 50 wt.%, more preferably in the range of about 1 wt.% to about 20 wt.%, of the total weight of the photosensitive layer 2b.

As the charge generating material 3, the following can be employed in the present invention: inorganic pigments, such as selenium, a selenium-tellurium alloy, cadmium sulfide, a cadmium sulfide-selenium alloy and α-silicon; and organic pigments, such as C.I. Pigment Blue 25 (C.I. 21180), C.I. Pigment Red 41 (C.I. 21200), C.I. Acid Red 52 (C.I. 45100) and C.I. Basic Red 3 (C.I. 45210); an azo pigment having a carbazole skeleton (Japanese Laid-Open Patent Application 53-95033), an azo dye having a distyryl-benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxazole skeleton (Japanese Laid-Open Patent Application 54-12742), an azo pigment having a fluorenon skeleton (Japanese Laid-Open Patent Application 54-22834), an azo pigment having a bisstilbene skeleton (Japanese Laid-Open Patent Application 54-17733). an azo pigment having a distyryl oxadiazole skeleton (Japanese Laid-Open Patent Application 54-2129), an azo dye having a distyryl carbazole skeleton (Japanese Laid-Open Patent Application 54-14967); a phthalocyanine-type pigment such as C.I. Pigment Blue 16 (C.I. 74100); Indigo-type pigments such as C.I. Vat Brown 5 (C.I. 73410) and C.I. Vat Dye (C.I.73030); and perylene-type pigments, such as Algo Scarlet B (made by Bayer Co., Ltd.) and Indanthrene Scarlet R (made by Bayer Co., Ltd). These charge generating materials can be used alone or in combination.

The photoconductor according to the present invention as shown in FIG. 6 can be prepared, for example, as follows. The charge generating material 3 is vacuum-evaporated on the electroconductive support material 1, or the charge generating material 3 in the form of fine particles is dispersed in a solution of a binder agent, the dispersion is applied to the electroconductive support material 1 and then dried, and, if necessary, the applied layer is subjected to buffing to make the surface smooth or to adjust the thickness of the layer to a predetermined thickness, whereby the charge generating layer 5 is formed. The charge transporting layer 6 is then formed on the charge generating derivatives and a binder agent to the charge generating layer 5 and then drying. In this photoconductor, the charge generating material 3 employed is the same as that employed in the photoconductor shown in FIG. 5.

It is preferable that the thickness of the charge generating layer 5 be less than about 5 μm, more preferably less than about 2 μm. It is preferable that the thickness of the charge transporting layer 6 be in the range of about 3 μm to about 50 μm, more preferably in the range of about 5 μm to about 20 μm. In the case where the charge generating layer 5 comprises the charge generating material 3 in the form of fine particles, dispersed in a binder agent, it is preferable that the amount of the charge generating material 3 in the charge generating layer 5 be in the range of about 10 wt.% to about 95 wt.% of the entire weight of the charge generating layer 5, more preferably in the range of about 50 wt.% to about 90 wt.%. Further, it is preferable that the amount of the styrene derivative contained in the charge transporting layer 6 be in the range of about 10 wt.% to about 95 wt.%, more preferably in the range of about 30 wt.% to about 90 wt.% of the total weight of the charge transporting layer 6.

As the electroconductive support material 1 for use in the present invention, a metal plate or metal foil, for example, made of aluminum, a plastic film on which a metal, for example, aluminum, is evaporated, or paper which has been treated so as to be electroconductive, can be employed.

As the binder agent for use in the present invention, condensation resins, such as polyamide, polyurethane, polyester, epoxy resin, polyketone and polycarbonate; and vinyl polymers such as polyvinylketone, polystyrene, poly-N-vinylcarbazole and polyacrylamide, can be used.

Other conventional electrically insulating and adhesive resins can be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive layer or a barrier layer can be interposed between the electroconductive support material and the photosensitive layer. The adhesive layer or the barrier layer can be made of, for example, polyamide, nitrocellulose or aluminum oxide. It is preferable that the thickness of the adhesive layer or barrier layer be about 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image. When necessary, the developed image can be transferred to a sheet of paper. The photoconductors according to the present invention have high photosensitivity and excellent flexibility.

Preparation of embodiments of an electrophotographic photoconductor according to the present invention will now be explained in detail by referring to the following examples.

EXAMPLE P-1

The following components were ground and dispersed in a ball mill to prepare a charge generating layer formation liquid:

|  | Parts by Weight |
|---|---|
| Diane Blue (C.I. Pigment Blue 25, C.I. 21180, a charge generating pigment) of the following formula (CG-1)) | 76 |
| 2% tetrahydrofuran solution of a polyester resin (Vylon 200 made by Toyobo Co., Ltd.) | 1,260 |
| Tetrahydrofuran | 3,700 |

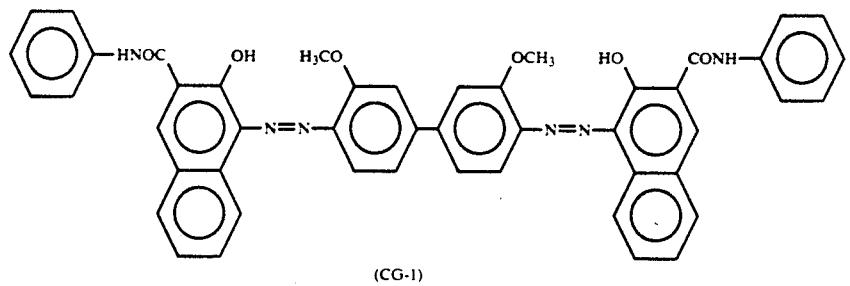

(CG-1)

The thus prepared charge generating layer formation liquid was applied by a doctor blade to the aluminum-evaporated surface of an aluminum-evaporated polyester base film, which served as an electroconductive support material, so that a charge generating layer having a thickness of about 1 μm when dried at room temperature was formed on the electroconductive support material.

Then the following components were mixed and dissolved, whereby a charge transporting layer formation liquid was prepared:

|  | Parts by Weight |
|---|---|
| Stilbene-type Derivative No. 6 in Table 2 | 2 |
| Polycarbonate resin (Panlite K 1300 made by Teijin Limited.) | 2 |
| Tetrahydrofuran | 16 |

The thus prepared charge transporting layer formation liquid was applied to the aforementioned charge generating layer by a doctor blade and was dried at 80° C. for 2 minutes and then at 105° C. for 5 minutes, so that a charge transporting layer with a thickness of about 20 μm was formed on the charge generating layer; thus, an electrophotographic photoconductor No. 1 according to the present invention was prepared.

The electrophotographic photoconductor No. 1 was charged negatively in the dark under application of −6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428) The photoconductor was then illuminated by a tungsten lamp in such a manner that the illuminance on the illuminated surface of the photoconductor was 20 lux, and the exposure $E_{\frac{1}{2}}$ (lux·seconds) required to reduce the initial surface potential Vpo (V) to $\frac{1}{2}$ the initial surface potential Vpo (V) was measured. The results showed that Vpo (V) = −1098 V and $E_{\frac{1}{2}}$ = 1.6 lux·seconds.

EXAMPLES P-2 THROUGH P-18

Example P-1 was repeated except that the charge generating material and the charge transporting material (Stilbene-type Derivative No. 6 in Table 2) employed in Example P-1 were respectively replaced by the charge generating materials and the charge transporting materials (stilbene-type derivatives) listed in Table 7, whereby electrophotographic photoconductors No. 2 through No. 18 according to the present invention were prepared.

Vpo and $E_{\frac{1}{2}}$ of the electrophotographic photoconductors No. 2 through No. 18 are shown in Table 8.

TABLE 7

| Photoconductor No. | Charge Generating Material | Charge Transporting Material Stilbene Type No. |
|---|---|---|
| 1 | (CG-1) | 6 |
| 2 | (CG-2) | 77 |
| 3 | (CG-3) | 22 |

TABLE 7-continued

| Photo-conductor No. | Charge Generating Material | Charge Transporting Material Stilbene Type No. |
|---|---|---|
| 4 | (CG-4) | 18 |
| 5 | (CG-5) | 2 |

TABLE 7-continued

| Photo-conductor No. | Charge Generating Material | Charge Transporting Material Stilbene Type No. |
|---|---|---|
| 6 | (structure shown) | 65 |
| | (CG-6) | |
| 7 | CG-3 | 45 |
| 8 | CG-5 | 74 |
| 9 | CG-3 | 33 |
| 10 | CG-5 | 19 |
| 11 | CG-3 | 58 |
| 12 | CG-5 | 88 |
| 13 | CG-3 | 94 |
| 14 | CG-5 | 37 |
| 15 | CG-3 | 24 |
| 16 | CG-5 | 64 |
| 17 | CG-3 | 60 |
| 18 | CG-5 | 79 |

EXAMPLE P-19

Selenium was vacuum-evaporated with a thickness of approximately 1.0 μm on an approximately 300 μm thick aluminum plate so that a charge generating layer was formed on the aluminum plate.

A charge transporting layer formation liquid was prepared by mixing and dispersing the following components:

|  | Parts by Weight |
|---|---|
| Stilbene-type derivative No. 22 in Table 2 | 2 |
| Polyester resin (Polyester Adhesive 49000 made by Du Pont Co.) | 3 |
| Tetrahydrofuran | 45 |

The thus prepared charge transporting layer formation liquid was applied to the aforementioned selenium charge generating layer by a doctor blade, dried at room temperature and then dried under reduced pressure, so that a charge transporting layer about 10 μm thick was formed on the charge generating layer, whereby an electrophotographic photoconductor No. 19 according to the present invention was prepared.

Vpo and $E_{\frac{1}{2}}$ were measured. The results showed that Vpo = −938 V and $E_{\frac{1}{2}}$ = 1.1 lux-seconds.

EXAMPLE P-20

A perylene pigment C.I. Vat Red 23 (C.I. 71130) of the following formula was vacuum-evaporated with a thickness of about 0.3 μm on an approximately 300 μm thick aluminum plate, whereby a charge generating layer was formed.

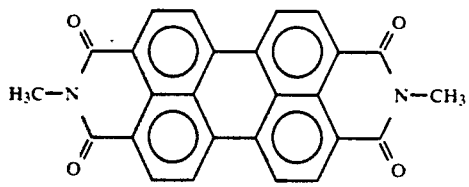

A charge transporting layer formation liquid was prepared by mixing and dispersing the following components:

|  | Parts by Weight |
|---|---|
| Stilbene-type derivative No. 66 in Table 2 | 2 |
| Polyester resin (Polyester Adhesive 49000 made by Du Pont Co.) | 3 |
| Tetrahydrofuran | 45 |

The thus prepared charge transporting layer formation liquid was applied to the aforementioned selenium charge generating layer by a doctor blade, dried at room temperature and then dried under reduced pressure, whereby a charge transporting layer about 10 μm thick was formed on the charge generating layer; thus, an electrophotographic photoconductor No. 20 according to the present invention was prepared.

Vpo and $E_{\frac{1}{2}}$ were measured. The results showed that Vpo = −1250 V and $E_{\frac{1}{2}}$ = 1.6 lux-seconds.

EXAMPLE P-21

One part by weight of Diane Blue (C.I. Pigment Blue 25, C.I. 21180) which was the same as that employed in Example P-1 was added to 158 parts by weight of tetrahydrofuran, and the mixture was ground and dispersed in a ball mill. To this mixture, 12 parts by weight of Stilbene-type styrene Derivative No. 84 and 18 parts by weight of a polyester resin (Polyester Adhesive 49000 made by Du Pont Co.) were added and mixed, whereby a photosensitive layer formation liquid was prepared.

The thus prepared photosensitive layer formation liquid was applied to an aluminum-evaporated polyester film by a doctor blade and was dried at 100° C. for 30 minutes, so that a photosensitive layer with a thickness of about 16 μm was formed on the aluminum-evaporated polyester film, whereby, an electrophotographic photoconductor No. 21 according to the present invention was prepared.

The electrophotographic photoconductor No. 21 was charged positively in the dark under application of +6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, so that the exposure $E_{\frac{1}{2}}$ (lux-seconds) required to reduce the initial surface potential Vpo (V) to ½ the initial surface potential Vpo (V) was measured. The results showed that Vpo (V) = +1206 V and $E_{\frac{1}{2}}$ = 1.5 lux-seconds.

The charge generating materials, the charge transporting materials, $V_{po}$ and $E_{\frac{1}{2}}$ of the electrophotographic photoconductors No. 1 through No. 21 are summarized in the following Table 8:

TABLE 8

| Photo-Conductor | Charge Generating Material | Charge Transporting Material (Stilbene-Type Derivative) | $V_{po}$ (V) | $E_{\frac{1}{2}}$ (lux · seconds) |
|---|---|---|---|---|
| No. 1 | CG-1 | No. 6 | −1098 | 1.6 |
| No. 2 | CG-2 | No. 77 | −945 | 1.4 |
| No. 3 | CG-3 | No. 33 | −901 | 1.2 |
| No. 4 | CG-4 | No. 18 | −980 | 1.9 |
| No. 5 | CG-5 | No. 2 | −990 | 0.7 |
| No. 6 | CG-6 | No. 65 | −784 | 0.9 |
| No. 7 | CG-3 | No. 45 | −948 | 1.5 |
| No. 8 | CG-5 | No. 74 | −1030 | 0.7 |
| No. 9 | CG-3 | No. 33 | −1240 | 1.4 |
| No. 10 | CG-5 | No. 19 | −1010 | 0.8 |
| No. 11 | CG-3 | No. 58 | −1120 | 1.3 |
| No. 12 | CG-5 | No. 88 | −970 | 0.8 |
| No. 13 | CG-3 | No. 94 | −925 | 0.9 |
| No. 14 | CG-5 | No. 37 | −1101 | 1.0 |
| No. 15 | CG-3 | No. 24 | −1240 | 1.5 |
| No. 16 | CG-5 | No. 64 | −1008 | 1.0 |
| No. 17 | CG-3 | No. 60 | −1152 | 1.1 |
| No. 18 | CG-5 | No. 79 | −1293 | 1.3 |
| No. 19 | selenium | No. 22 | −938 | 1.1 |
| No. 20 | Perylene-type Pigment | No. 66 | −1250 | 1.6 |
| No. 21 | CG-1 | No. 84 | +1206 | 1.5 |

EXAMPLE P-22

The following components were ground and dispersed in a ball mill to prepare a charge generating layer formation liquid:

|  | Parts by Weight |
| --- | --- |
| Diane Blue (C.I. Pigment Blue 25, C.I. 21180, the charge generating pigment CG-1) | 76 |
| 2% tetrahydrofuran solution of a polyester resin (Vylon 200 made by Toyobo Co., Ltd.) | 1,260 |
| Tetrahydrofuran | 3,700 |

The thus prepared charge generating layer formation liquid was applied by a doctor blade to the aluminum-evaporated surface of an aluminum-evaporated polyester base film, which served as an electroconductive support material, so that a charge generating layer having a thickness of about 1 μm when dried at room temperature was formed on the electroconductive support material.

Then the following components were mixed and dissolved, whereby a charge transporting layer formation liquid was prepared:

|  | Parts by Weight |
| --- | --- |
| Thiophene-type Derivative No. 102 in Table 4 | 2 |
| Polycarbonate resin (Panlite K 1300 made by Teijin Limited.) | 2 |
| Tetrahydrofuran | 16 |

The thus prepared charge transporting layer formation liquid was applied to the aforementioned charge generating layer by a doctor blade and was dried at 80° C. for 2 minutes and then at 105° C. for 5 minutes, so that a charge transporting layer with a thickness of about 20 μm was formed on the charge generating layer; thus, an electrophotographic photoconductor No. 22 according to the present invention was prepared.

Vpo and $E_{\frac{1}{2}}$ were measured. The results showed that Vpo (V) = −935 V and $E_{\frac{1}{2}}$ = 1.3 lux·seconds.

EXAMPLES P-23 THROUGH P-37

Example P-22 was repeated except that the charge generating material and the charge transporting material (Thiophene-type Derivative No. 102 in Table 4) employed in Example P-22 were respectively replaced by the charge generating materials and the charge transporting materials (thiophene-type derivatives) listed in Table 9, whereby electrophotographic photoconductors No. 22 through No. 37 according to the present invention were prepared.

Vpo and $E_{\frac{1}{2}}$ of the electrophotographic photoconductors No. 22 through No. 37 are shown in Table 10.

TABLE 9

| Photoconductor No. | Charge Generating Material | Charge Transporting Material Thiophene Type No. |
|---|---|---|
| 22 | (CG-1) | 102 |
| 23 | (CG-2) | 108 |
| 24 | (CG-3) | 112 |

TABLE 9-continued

| Photo-conductor No. | Charge Generating Material | Charge Transporting Material Thiophene Type No. |
|---|---|---|
| 25 | (CG-4) | 118 |
| 26 | (CG-5) | 126 |

TABLE 9-continued
| Photo-conductor No. | Charge Generating Material | Charge Transporting Material Thiophene Type No. |
|---|---|---|
| 27 | 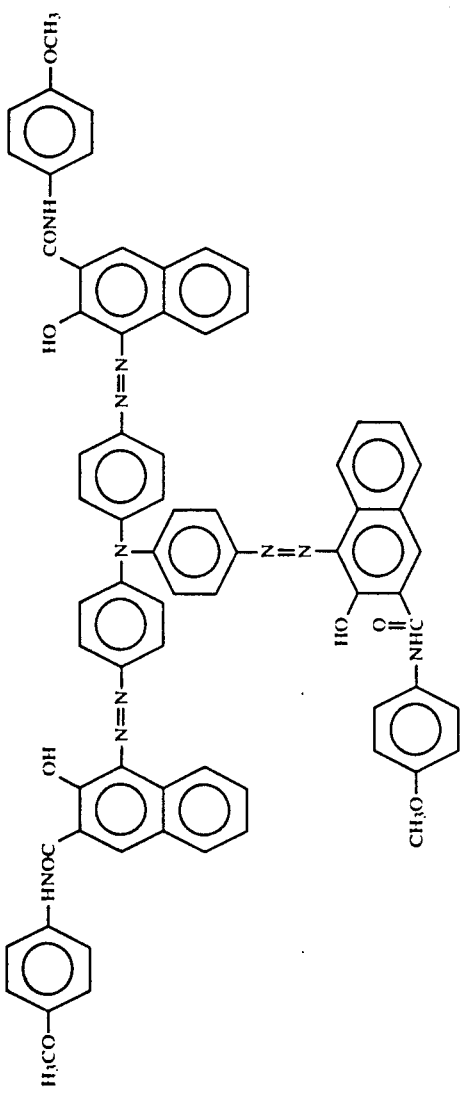 | 128 |
| 28 | CG-3 | 132 |
| 29 | CG-5 | 116 |
| 30 | CG-3 | 98 |
| 31 | CG-5 | 103 |
| 32 | CG-3 | 124 |
| 33 | CG-5 | 119 |
| 34 | CG-3 | 125 |
| 35 | CG-5 | 131 |
| 36 | CG-3 | 130 |
| 37 | CG-5 | 135 |
(CG-6)

EXAMPLE P-38

Selenium was vacuum-evaporated with a thickness of approximately 1.0 μm on an approximately 300 μm thick aluminum plate so that a charge generating layer was formed on the aluminum plate.

A charge transporting layer liquid was prepared by mixing and dispersing the following components:

|  | Parts by Weight |
|---|---|
| Thiophene-type Derivative No. 133 in Table 4 | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then dried under reduced pressure, so that a charge transporting layer about 10 μm thick was formed on the charge generating layer; thus, an electrophotographic photoconductor No. 38 according to the present invention was prepared.

$V_{po}$ and $E_{\frac{1}{2}}$ were measured. The results showed that $V_{po} = -681$ V and $E_{\frac{1}{2}} = 0.9$ lux·seconds.

EXAMPLE P-39

A perylene pigment C.I. Vat Red 23 (C.I. 71130) of the following formula was vacuum-evaporated with a thickness of about 0.3 μm on an approximately 300 μm thick aluminum plate so that a charge generating layer was formed.

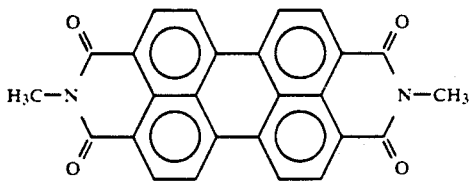

A charge transporting layer liquid was prepared by mixing and dispersing the following components:

|  | Parts by Weight |
|---|---|
| Thiophene-type Derivative No. 117 in Table 4 | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then dried under reduced pressure, whereby a charge transporting layer about 10 μm thick was formed on the charge generating layer; thus, an electrophotographic photoconductor No. 39 according to the present invention was prepared.

$V_{po}$ and $E_{\frac{1}{2}}$ were measured. The results showed that $V_{po} = -965$ V and $E_{\frac{1}{2}} = 1.1$ lux·seconds.

EXAMPLE P-40

One part by weight of Diane Blue (C.I. Pigment Blue 25, C.I. 21180) which was the same as that employed in Example P-1 was added to 158 parts by weight of tetrahydrofuran, and the mixture was ground and dispersed in a ball mill. To this mixture, 12 parts by weight of Thiophene-type Derivative No. 107 and 18 parts by weight of a polyester resin (Polyester Adhesive 49000 made by Du Pont Co.) were added and mixed, whereby a photosensitive layer formation liquid was prepared.

The thus prepared photosensitive layer formation liquid was applied to an aluminum-evaporated polyester film by a doctor blade and was dried at 100° C. for 30 minutes, so that a photosensitive layer with a thickness of about 16 μm was formed on the aluminum-evaporated polyester film, whereby, an electrophotographic photoconductor No. 40 according to the present invention was prepared.

The electrophotographic photoconductor No. 40 was charged positively in the dark under application of +6 kV of corona charge, and $V_{po}$ and $E_{\frac{1}{2}}$ of this photoconductor were measured in the same manner as in Example P-21. The results showed that $V_{po}$ (V) = +892 V and $E_{\frac{1}{2}}$ = 1.2 lux·seconds.

The charge generating material, the charge transporting material, $V_{po}$ and $E_{\frac{1}{2}}$ of each of the electrophotographic photoconductors No. 22 through No. 40 are summarized in the following Table 10:

TABLE 10

| Photo-Conductor | Charge Generating Material | Charge Transporting Material (Stilbene-Type Derivative) | $V_{po}$ (V) | $E_{\frac{1}{2}}$ (lux · seconds) |
|---|---|---|---|---|
| No. 22 | CG-1 | No. 102 | −935 | 1.3 |
| No. 23 | CG-2 | No. 108 | −783 | 1.2 |
| No. 24 | CG-3 | No. 112 | −832 | 1.2 |
| No. 25 | CG-4 | No. 118 | −691 | 0.9 |
| No. 26 | CG-5 | No. 126 | −1100 | 0.8 |
| No. 27 | CG-6 | No. 128 | −1376 | 1.3 |
| No. 28 | CG-3 | No. 132 | −1240 | 1.3 |
| No. 29 | CG-5 | No. 116 | −1011 | 1.4 |
| No. 30 | CG-3 | No. 98 | −1170 | 1.1 |
| No. 31 | CG-5 | No. 103 | −990 | 0.7 |
| No. 32 | CG-3 | No. 124 | −1265 | 1.3 |
| No. 33 | CG-5 | No. 119 | −1030 | 1.1 |
| No. 34 | CG-3 | No. 125 | −934 | 1.1 |
| No. 35 | CG-5 | No. 131 | −882 | 0.9 |
| No. 36 | CG-3 | No. 130 | −1033 | 1.0 |
| No. 37 | CG-5 | No. 135 | −1280 | 1.2 |
| No. 38 | Selenium | No. 133 | −681 | 0.9 |
| No. 39 | Perylene-type Pigment | No. 117 | −965 | 1.1 |
| No. 40 | CG-1 | No. 107 | +892 | 1.2 |

EXAMPLE P-41

The following components were ground and dispersed in a ball mill to prepare a charge generating layer formation liquid:

|  | Parts by Weight |
|---|---|
| Diane Blue (C.I. Pigment Blue 25, C.I. 21180, the charge generating pigment CG-1) | 76 |
| 2% tetrahydrofuran solution of a polyester resin (Vylon 200 made by Toyobo Co., Ltd.) | 1,260 |
| Tetrahydrofuran | 3,700 |

The thus prepared charge generating layer formation liquid was applied by a doctor blade to the aluminum-evaporated surface of an aluminum-evaporated polyester base film, which served as an electroconductive support material, so that a charge generating layer having a thickness of about 1 μm when dried at room temperature was formed on the electroconductive support material.

Then the following components were mixed and dissolved, whereby a charge transporting layer formation liquid was prepared:

| | Parts by Weight |
|---|---|
| Naphtharene-type Derivative No. 147 in Table 6 | 2 |
| Polycarbonate resin (Panlite K 1300 made by Teijin Limited.) | 2 |
| Tetrahydrofuran | 16 |

The thus prepared charge transporting layer formation liquid was applied to the aforementioned charge generating layer by a doctor blade and was dried at 80° C. for 2 minutes and then at 105° C. for 5 minutes, so that a charge transporting layer with a thickness of about 20 μm was formed on the charge generating layer, whereby an electrophotographic photoconductor No. 41 according to the present invention was prepared.

Vpo and $E_{\frac{1}{2}}$ of the electrophotographic photoconductor No. 41 were measured. The results showed that Vpo (V) = −1120 V and $E_{\frac{1}{2}}$ = 2.0 lux-seconds.

EXAMPLES P-42 THROUGH P-58

Example P-41 was repeated except that the charge generating material and the charge transporting material (Naphthalene-type Derivative No. 147 in Table 6) employed in Example P-41 were respectively replaced by the charge generating materials and the charge transporting materials (naphthalene-type derivatives) listed in Table 11, whereby electrophotographic photoconductors No. 42 through No. 58 according to the present invention were prepared.

Vpo and $E_{\frac{1}{2}}$ of the electrophotographic photoconductors No. 42 through No. 58 are shown in Table 12.

TABLE 11

| Photo-conductor No. | Charge Generating Material | Charge Transporting Material Naphthalene Type No. |
| --- | --- | --- |
| 41 | (CG-1) | 145 |
| 42 | (CG-2) | 147 |
| 43 | (CG-3) | 182 |

TABLE 11-continued

| Photo-conductor No. | Charge Generating Material | Charge Transporting Material Naphthalene Type No. |
|---|---|---|
| 44 | (CG-4) | 163 |
| 45 | (CG-5) | 205 |

TABLE 11-continued
| Photo-conductor No. | Charge Generating Material | Charge Transporting Material Naphthalene Type No. |
|---|---|---|
| 46 | 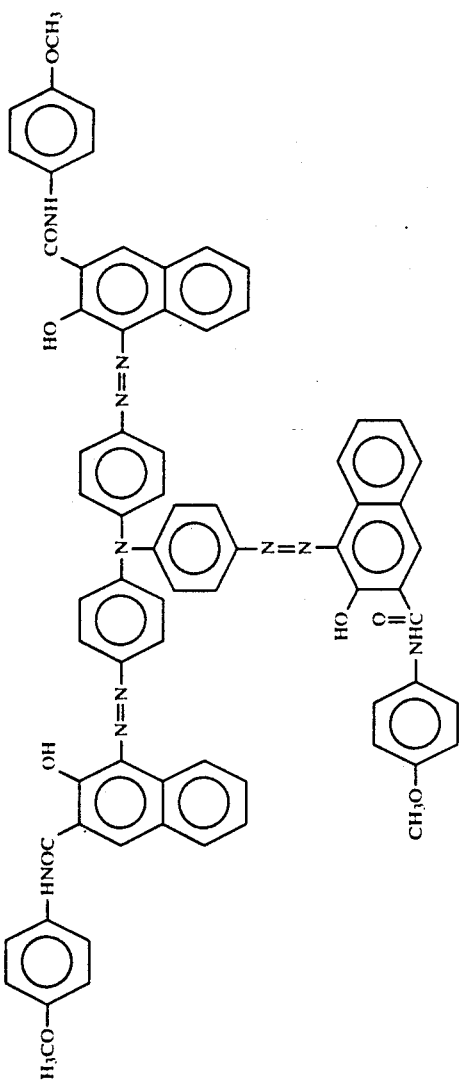 | 199 |
| 47 | CG-3 | 143 |
| 48 | CG-5 | 170 |
| 49 | CG-3 | 195 |
| 50 | CG-5 | 159 |
| 51 | CG-3 | 149 |
| 52 | CG-5 | 174 |
| 53 | CG-3 | 161 |
| 54 | CG-5 | 172 |
| 55 | CG-3 | 200 |
| 56 | CG-5 | 187 |
| 57 | CG-3 | 158 |
| 58 | CG-5 | 153 |
(CG-6)

EXAMPLE P-59

Selenium was vacuum-evaporated with a thickness of approximately 1.0 μm on an approximately 300 μm thick aluminum plate so that a charge generating layer was formed on the aluminum plate.

A charge transporting layer liquid was prepared by mixing and dispersing the following components:

| | Parts by Weight |
|---|---|
| Naphthalene-type derivative No. 162 in Table 6 | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then dried under reduced pressure, so that a charge transporting layer about 10 μm thick was formed on the charge generating layer, whereby an electrophotographic photoconductor No. 59 according to the present invention was prepared.

$V_{po}$ and $E_{\frac{1}{2}}$ were measured. The results showed that $V_{po} = -834$ V and $E_{\frac{1}{2}} = 1.4$ lux-seconds.

EXAMPLE P-60

A perylene pigment C.I. Vat Red 23 (C.I. 71130) of the following formula was vacuum-evaporated with a thickness of about 0.3 μm on an approximately 300 μm thick aluminum plate so that a charge generating layer was formed.

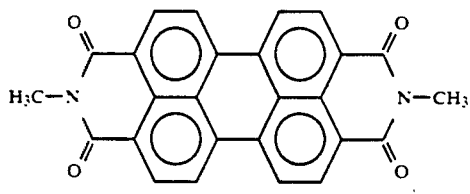

A charge transporting layer liquid was prepared by mixing and dispersing the following components:

| | Parts by Weight |
|---|---|
| Naphthalene-type Derivative No. 153 in Table 6 | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then dried under reduced pressure, whereby a charge transporting layer about 10 μm thick was formed on the charge generating layer; thus, an electrophotographic photoconductor No. 20 according to the present invention was prepared.

$V_{po}$ and $E_{\frac{1}{2}}$ were measured. The results showed that $V_{po} = -961$ V and $E_{\frac{1}{2}} = 1.3$ lux-seconds.

EXAMPLE P-61

One part by weight of Diane Blue (C.I. Pigment Blue 25, C.I. 21180) which was the same as that employed in Example P-1 was added to 158 parts by weight of tetrahydrofuran, and the mixture was ground and dispersed in a ball mill. To this mixture, 12 parts by weight of Naphthalene-type styrene Derivative No. 190 and 18 parts by weight of a polyester resin (Polyester Adhesive 49000 made by Du Pont Co.) were added and mixed, whereby a photosensitive layer formation liquid was prepared.

The thus prepared photosensitive layer formation liquid was applied to an aluminum-evaporated polyester film by a doctor blade and was dried at 100° C. for 30 minutes, so that a photosensitive layer with a thickness of about 16 μm was formed on the aluminum-evaporated polyester film, whereby, an electrophotographic photoconductor No. 61 according to the present invention was prepared.

The electrophotographic photoconductor No. 61 was charged positively in the dark under application of +6 kV of corona charge, and $V_{po}$ and $E_{\frac{1}{2}}$ of this photoconductor were measured in the same manner as in Example P-21. The results showed that $V_{po}$ (V) = +1206 V and $V_{\frac{1}{2}}$ = 1.5 lux-seconds.

The charge generating material, the charge transporting material, $V_{po}$ and $E_{\frac{1}{2}}$ of each of the electrophotographic photoconductors No. 41 through No. 61 are summarized in the following Table 12:

TABLE 12

| Photo-Conductor | Charge Generating Material | Charge Transporting Material (Naphthalene-Type Derivative) | $V_{po}$ (V) | $E_{\frac{1}{2}}$ (lux · seconds) |
|---|---|---|---|---|
| No. 41 | CG-1 | No. 145 | −1120 | 2.0 |
| No. 42 | CG-2 | No. 147 | −1002 | 2.4 |
| No. 43 | CG-3 | No. 182 | −1050 | 1.4 |
| No. 44 | CG-4 | No. 163 | −1218 | 1.9 |
| No. 45 | CG-5 | No. 205 | −931 | 1.2 |
| No. 46 | CG-6 | No. 199 | −1159 | 1.5 |
| No. 47 | CG-3 | No. 143 | −1080 | 0.9 |
| No. 48 | CG-5 | No. 170 | −1100 | 1.0 |
| No. 49 | CG-3 | No. 195 | −985 | 1.1 |
| No. 50 | CG-5 | No. 159 | −1025 | 0.7 |
| No. 51 | CG-3 | No. 149 | −1110 | 1.1 |
| No. 52 | CG-5 | No. 174 | −1020 | 0.9 |
| No. 53 | CG-3 | No. 161 | −896 | 1.0 |
| No. 54 | CG-5 | No. 172 | −980 | 1.3 |
| No. 55 | CG-3 | No. 200 | −1421 | 1.7 |
| No. 56 | CG-5 | No. 187 | −1433 | 1.1 |
| No. 57 | CG-3 | No. 158 | −1011 | 1.6 |
| No. 58 | CG-5 | No. 153 | −997 | 1.0 |
| No. 59 | Selenium | No. 162 | −834 | 1.4 |
| No. 60 | Perylene-type Pigment | No. 153 | −961 | 1.6 |
| No. 61 | CG-1 | No. 190 | +1136 | 1.9 |

Each of the electrophotographic photoconductors prepared in Example P-1 through P-20, P-22 through P-39, and P-41 through P-60 was negatively charged, while the electrophotographic photoconductors prepared in Examples P-21, P-40 and P-61 were positively charged, by a commercially available copying machine, so that a latent electrostatic image was formed on each photoconductor and electrostatic image was formed on each photoconductor and was developed with a dry type developer. The developed images were transferred to a high quality transfer sheet and were fixed to the transfer sheet. As a result, clear images were obtained from each of the electrophotographic photoconductors.

When a wet type developer was used instead of the dry type developer, a clear image was also obtained from each of the electrophotographic photoconductors.

What is claimed is:

1. A styrene derivative of the formula:

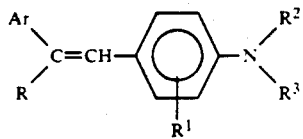

wherein $R^1$ represents a lower alkyl or a lower alkoxy group; and $R^2$ and $R^3$ each represent a lower alkyl group, an aralkyl group, or an unsubstituted or substituted phenyl group, with the provision that at least one of $R^2$ and $R^3$ is an aralkyl group, or an unsubstituted or substituted phenyl group; Ar is a lower alkyl-, lower alkoxy-, halogen-substituted phenyl or styryl group, or an unsubstituted phenyl or styryl group; R represents hydrogen, a lower alkyl group, or an unsubstituted or lower alkyl-, lower alkoxy- or halogen-substituted phenyl group, with the provision that when Ar is an unsubstituted styryl group, R is not hydrogen, the substituent on said substituted phenyl group of $R^2$ and $R^3$ being selected from the group consisting of alkyl, alkoxy, aryloxy, aralkyloxy, thioalkoxy, thiophenyl, halogen, dialkylamino, hydroxy, acyl, carboxy, carboxy ester, trifluoromethyl, nitro and cyano.

2. A styrene derivative as claimed in claim 1, which is 2-methyl-4-N,N-diphenylamino-β-phenylstilbene.

* * * * *

UNITED STATES PATENT AND TRADEMARK OFFICE
CERTIFICATE OF CORRECTION

PATENT NO. : 5,072,043

DATED : December 10, 1991

INVENTOR(S) : Masayuki Shoshi, et al

It is certified that error appears in the above-indentified patent and that said Letters Patent is hereby corrected as shown below:

Column 1, line 59, reads "photo-conductors", should read --photoconductors--;

Column 2, line 10, reads "poly N-vinylcarbazole", should read --poly-N-vinylcarbazole--;

Column 2, line 56, Between second and third formulas, reads "and", should read --or--;

Column 3, line 6, reads "(ß-8-phenylstyryl)", should read --(ß-phenylstyryl)--

Column 3, line 26, reads "above mentioned", should read --above-mentioned--;

Column 6, line 14, reads "point was 119.5 121.0C̊", should read --point was 119.5-121.0C̊--;

Column 6, lines 19-20, read "diphenylamino-8 - phenylstlbene", should read --diphenylamino-ß-phenylstilbene--;

Column 7, line 17, reads "diphenyl-aminobenzaldehyde", should read --diphenylaminobenzaldehyde--;

Column 29, lines 51-52, read "(8-phenylstyryl)", should read --(ß-phenylstyryl)--;

Column 29, line 59, reads "were were as follows:", should read --were as follows:--;

UNITED STATES PATENT AND TRADEMARK OFFICE
CERTIFICATE OF CORRECTION

PATENT NO. : 5,072,043

DATED : December 10, 1991

INVENTOR(S) : Masayuki Shoshi et al

It is certified that error appears in the above-indentified patent and that said Letters Patent is hereby corrected as shown below:

Column 29, line 67; reads "(8-phenylstyryl)", should read --(ß-phenylstyryl)--;

Columns 31-32, line 62, reads

"                                                                                      "

105    CH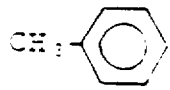    H    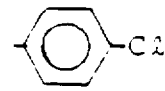Cl    

should read --

105    CH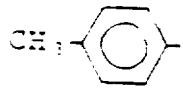    H    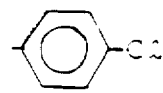Cl    

--

Column 40, line 59, reads "propoxy and butoxty;", should read --propoxy and butoxy--;

UNITED STATES PATENT AND TRADEMARK OFFICE
CERTIFICATE OF CORRECTION

PATENT NO. : 5,072,043
DATED : December 10, 1991
INVENTOR(S) : Masayuki Shoshi et al It is certified that error appears in the above-indentified patent and that said Letters Patent is hereby corrected as shown below:

Column 41, line 22, reads "(8-phenylstyryl)", should read --(ß-phenylstyryl)--;

Column 42, line 2, reads "(8-phenylstyryl)", should read --(ß-phenylstyryl)--;

Column 42, line 11, reads "(8-phenylstyryl", should read --(ß-phenylstyryl)--;

Column 42, line 14, reads "(or 8-phenylstyryl-4-N,", should read --(or ß-phenylstyryl-4-N,--;

Column 50, reads

"

166   = 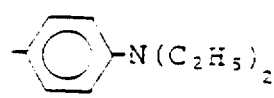 

"

should read

--

166   = 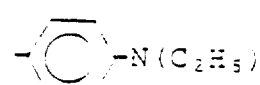 

UNITED STATES PATENT AND TRADEMARK OFFICE
CERTIFICATE OF CORRECTION

PATENT NO. : 5,072,043
DATED : December 10, 1991
INVENTOR(S) : Masayuki Shoshi, et al It is certified that error appears in the above-indentified patent and that said Letters Patent is hereby corrected as shown below:

Column 59, lines 708, read "cros-ssectional", should read --cross-sectional--;

Column 59, lines 39-40, read "cros-ssectional", should read --cross-sectional--;

Column 60, line 59, reads "a distyryl-benzene skeleton", should read --a distyrylbenzene skeleton--;

Column 61, line 25, reads "generating derivatives and a", should read --generating layer 5 by applying a solution of one or more styrene derivatives and a--;

Column 91, line 60, reads "No.20", should read -- No.60--;

UNITED STATES PATENT AND TRADEMARK OFFICE
CERTIFICATE OF CORRECTION

PATENT NO. : 5,072,043

DATED : December 10, 1991

INVENTOR(S) : Masayuki Shoshi et al

It is certified that error appears in the above-indentified patent and that said Letters Patent is hereby corrected as shown below:

Column 92, line 21, reads "(V)=+1206 V and $V_{\frac{1}{2}}$=1.5 lux·seconds.--, should read --(V)=+1206 V and $E_{\frac{1}{2}}$=1.5 lux·seconds.

Signed and Sealed this

Eighteenth Day of October, 1994

Attest:

BRUCE LEHMAN

Attesting Officer

Commissioner of Patents and Trademarks